US008628779B2

(12) United States Patent
Preville et al.

(10) Patent No.: US 8,628,779 B2
(45) Date of Patent: Jan. 14, 2014

(54) RECOMBINANT PROTEIN CARRYING HUMAN PAPILLOMAVIRUS EPITOPES INSERTED IN AN ADENYLATE CYCLASE PROTEIN OR FRAGMENT THEREOF. THERAPEUTIC USES THEREOF

(75) Inventors: Xavier-Edmond-Edouard Preville, Pins Justaret (FR); Claude Leclerc, Paris (FR); Daniel Ladant, Cachan (FR); Benedikt Timmerman, Toulouse (FR)

(73) Assignees: Institut Pasteur, Paris (FR); Genticel, Labege-Innopole (FR); Institut National de la Sante et de la Recherche Medicale, Paris (FR); Centre National de la Recherche Scientifique, Paris (FR)

( * ) Notice: Subject to any disclaimer, the term of this patent is extended or adjusted under 35 U.S.C. 154(b) by 1147 days.

(21) Appl. No.: 11/517,313

(22) Filed: Sep. 8, 2006

(65) Prior Publication Data
US 2007/0072266 A1 Mar. 29, 2007

Related U.S. Application Data

(63) Continuation of application No. PCT/EP2005/003452, filed on Mar. 18, 2005.

(30) Foreign Application Priority Data

Mar. 18, 2004 (EP) .................................... 04290741

(51) Int. Cl.
*A61K 39/12* (2006.01)
*A61K 39/295* (2006.01)
*C07K 14/235* (2006.01)
*C07K 14/025* (2006.01)

(52) U.S. Cl.
USPC ................... 424/185.1; 424/186.1; 424/192.1; 435/5; 530/350

(58) Field of Classification Search
None
See application file for complete search history.

(56) References Cited

U.S. PATENT DOCUMENTS

| 6,183,745 B1 | 2/2001 | Tindle et al. | |
|---|---|---|---|
| 2003/0157135 A1* | 8/2003 | Tsuji et al. | 424/278.1 |
| 2004/0001867 A1* | 1/2004 | Leclerc et al. | 424/253.1 |
| 2005/0271679 A1 | 12/2005 | Dadaglio et al. | |
| 2008/0152665 A1 | 6/2008 | Leclerc et al. | |
| 2010/0150999 A1 | 6/2010 | Leclerc et al. | |
| 2010/0310594 A1 | 12/2010 | Dadeglio et al. | |
| 2011/0171244 A1 | 7/2011 | Preville et al. | |

FOREIGN PATENT DOCUMENTS

| EP | 0 456 197 A1 | 11/1991 | |
|---|---|---|---|
| EP | 00402562.3 | 3/2002 | |
| EP | 04290741.0 | 9/2007 | |
| EP | 06291393.4 | 3/2008 | |
| EP | 09155929.4 | 9/2010 | |
| ER | 03291486.3 | 12/2004 | |
| WO | WO 91/18294 | * 11/1991 | ........... G01N 33/569 |
| WO | WO 93/21324 | 10/1993 | |

OTHER PUBLICATIONS

Saron et al. Proc. Natl. Acad. Sci. USA, Apr. 1997, vol. 94, No. 7, pp. 3314-3319.*
Guermonprez et al. Journal of Experimental Medicine, May 2001, vol. 193, No. 9, pp. 1035-1044.*
Krul et al. Cancer Immunology Immunotherapy, Oct. 1996, vol. 43, No. 1, pp. 44-48.*
Fayolle C et al. Delivery of multiple epitopes by recombinant detoxified adenylate cyclase of Bordetella pertussis induces protective antiviral immunity. J Virol. Aug. 2001;75(16):7330-8.*
Baldwin PJ et al. Vaccinia-expressed human papillomavirus 16 and 18 e6 and e7 as a therapeutic vaccination for vulval and vaginal intraepithelial neoplasia. Clin Cancer Res. Nov. 1, 2003;9(14):5205-13.*
Castellanos MR, Hayes RL, Maiman MA. Gynecol Oncol. Jul. 2001;82(1):77-83.*
Kim SJ et al. Enhanced immunogenicity of human papillomavirus 16 L1 genetic vaccines fused to an ER-targeting secretory signal peptide and RANTES. Gene Ther. Aug. 2003;10(15):1268-73.*
Todd RW et al. Human papillomavirus (HPV) type 16-specific CD8+ T cell responses in women with high grade vulvar intraepithelial neoplasia. Int J Cancer. Mar. 1, 2004;108(6):857-62.*
Sebo, et al., "Cell-Invasive Activity of Epitope-Tagged Adenylate Cyclase of Bordetella pertussis Allows in Vitro Presentation of a Foreign Epitope to CD8+ Cytotoxic T Cells", Infection and Immunity, American Society for Microbiology, XP-000770792, vol. 63, No. 10, pp. 3851-3857, (Oct. 1, 1995).
Giannouli, et al., "Fusion of a Tumour-associated Antigen to HIV-1 Tat Improves Protein-based Immunotherapy of Cancer", Anticancer Research, Helenic Anticancer Institute, XP-009031082, vol. 23, No. 4, pp. 3523-3532, (Jul. 4, 2003).
Jansen, et al., "Human Papillomavirus Vaccines and Prevention of Cervical Cancer", Annual Review of Medicine, XP-009031083, vol. 55, pp. 319-331, (2004).
Gunn, et al., "Two *Listeria monocytogenes* Vaccine Vectors That Express Different Molecular Forms of Human Papilloma Virus-16 (HPV-16) E7 Induce Qualitatively Different T Cell Immunity That Correlates with Their Ability to Induce Regression of Established Tumors Immortalized by HPV-16¹", Journal of Immunology, XP-002289027, vol. 167, No. 11, pp. 6471-6479, (Dec. 1, 2001).
Fayolle, et al., "Delivery of Multiple Epitopes by Recombinant Detoxified Adenylate Cyclase of *Bordetella pertussis* Induces Protective Antiviral Immunity", Journal of Virology, XP-002209814, vol. 75, No. 16, pp. 7330-7338, (Aug. 2001).

(Continued)

*Primary Examiner* — Louise Humphrey
*Assistant Examiner* — Nick Zou
(74) *Attorney, Agent, or Firm* — Law Office of Salvatore Arrigo and Scott Lee, LLP

(57) ABSTRACT

The invention relates to a recombinant protein comprising one or several polypeptides bearing one or several epitopes of one or several HPV antigens, said polypeptides being inserted in the same or different permissive sites of an adenylate cyclase (CyaA) protein or of a fragment thereof, wherein said CyaA fragment retains the property of said adenylate cyclase protein to target Antigen Presenting Cells. It also concerns polynucleotides encoding the same. The recombinant protein or the polynucleotide can be used for the design of therapeutic means against HPV infection or against its malignant effects.

43 Claims, 21 Drawing Sheets

(56) References Cited

OTHER PUBLICATIONS

Figure 1:
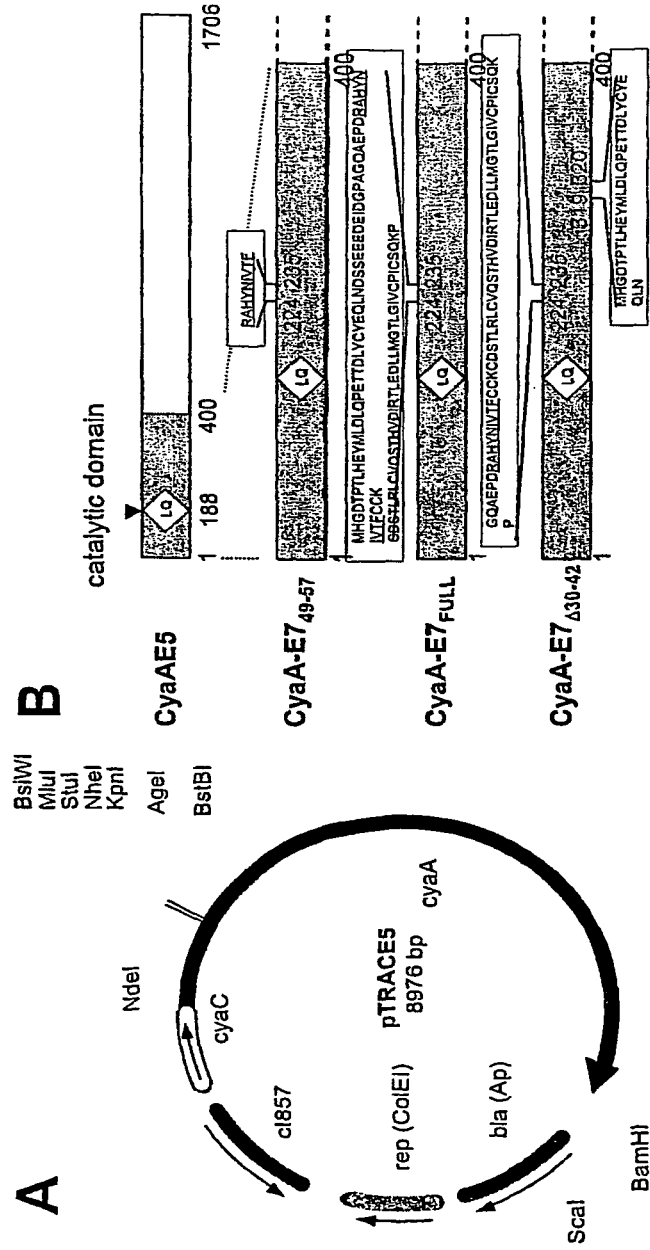
Figure 1:

Fayolle, et al., "Therapy of Murine Tumors with Recombinant *Bordetella pertussis* Adenylate Cyclase Carrying a Cytoxic T Cell Epitope[1]", Journal of Imunology, XP-002169918, vol. 162, pp. 4157-4162, (1999).

Karimova, et al., "Charge-dependent translocation of *Bordetella pertussis* adenylate cyclase toxin into eukaryotic cells: Implication for the in vivo delivery of CD8[+] T Cell epitopes into antigen-presenting cells", Proceedings of the National Academy of Sciences of the United States of America, XP-002289028, vol. 95, No. 21, pp. 12532-12537, (Oct. 13, 1998).

Saron, et al., "Anti-viral protection conferred by recombinant adenylate cyclase toxins from *Bordetella pertussis* carrying a CD8+ T cell epitope from lymphocytic choriomeningitis virus", Proceedings of the National Academy of Sciences of the United States of America, XP-002289029, vol. 94, No. 7, pp. 3314-3319, (Apr. 1997).

Osička, et al., "Delivery of $CD8^+$ T-Cell Epitopes into Major Histocompatibility Complex Class I Antigen Presentation Pathway by *Bordetella pertussis* Adenylate Cyclase: Delineation of Cell Invasive Structures and Permissive Insertion Sites", Infection and Immunity, American Society for Microbiology, XP-002263297, vol. 68, No. 1, pp. 247-256, (Jan. 2000).

Mohammed El-Azami-El-Idrissi, et al., "Interaction of *Bordetella pertussis* Adenylate Cyclase with CD11b/CD18—Role of Toxin Acylation and Identification of the Main Integrin Interaction Domain", Journal of Biological Chemistry, XP-002289030, vol. 278, No. 40, pp. 38514-38521, (Oct. 3, 2003).

Chu, et al.; Immunotherapy of a human papillomavirus (HPV) type 16 E7-expressing tumour by administration of fusion protein comprising *Mycobacterium bovis* bacille Calmette-Guérin (BCG) hsp65 and HPV16 E7; Clin Exp Immunol. vol. 121, 2000, pp. 216-225.

Dadaglio, et al.; Induction of a Polarized Th1 Response by Insertion of Multiple Copies of a Viral T-Cell Epitope into Adenylate Cyclase of *Bordetella pertussis*; Infect. Immun., vol. 68, No. 7, Jul. 2000, pp. 867-3872.

Dadaglio, et al.; Recombinant adenylate cyclase toxin of *Bordetella pertussis* induces cytotoxic T lymphocyte responses against HLA*0201-restricted melanoma epitopes; Intern. Immunol., vol. 15, No. 12, 2003, pp. 1423-1430.

European Search Report in corresponding EP application EP 05 72 8249.3.

Feltkamp, et al.; Vaccination with cytotoxic T lymphocyte epitope-containing peptide protects against a tumor induced by human papillomavirus type 16-transformed cells; Eur. J. Immunol., vol. 23, 1993, pp. 2242-2249.

Liu, et al.; Recombinant Adeno-Associated Virus Expressing Human Papillomavirus Type 16 E7 Peptide DNA Fused with Heat Shock Protein DNA as a Potential Vaccine for Cervical Cancer; J. Virol., vol. 74, No. 6, 2000, pp. 2888-2894.

Saron, et al.; Anti-viral protection conferred by recombinant adenylate cyclase toxins from *Bordetella pertussis* carrying a CD8+ T cell epitope from lymphocytic choriomeningitis virus; PNAS, vol. 94, No. 7, 1997, pp. 3314-3319.

Office Action dated Oct. 14, 2010 in U.S. Appl. No. 11/778,267.

Office Action dated Apr. 19, 2011 in U.S. Appl. No. 12/439,379.

USPTO, Decision on Appeal, Jan. 25, 2010, in U.S. Appl. No. 10/994,204.

U.S. Appl. No. 10/994,204, Examiner's Answer dated Aug. 19, 2008.

U.S. Appl. No. 10/994,204, Office Action dated May 31, 2007.

U.S. Appl. No. 10/994,204, Office Action dated Oct. 20, 2006.

U.S. Appl. No. 11/778,267, Office Action dated Feb. 16, 2010.

U.S. Appl. No. 11/778,267, Office Action dated Oct. 14, 2010.

U.S. Appl. No. 12/439,379, Office Action dated Mar. 29, 2012.

U.S. Appl. No. 12/439,379, Office Action dated Sep. 29, 2011.

U.S. Appl. No. 12/731,196, Office Action dated Apr. 30, 2013.

U.S. Appl. No. 12/731,196, Office Action dated Jan. 23, 2012.

U.S. Appl. No. 12/731,196, Office Action dated Jun. 14, 2012.

* cited by examiner

Figure 2
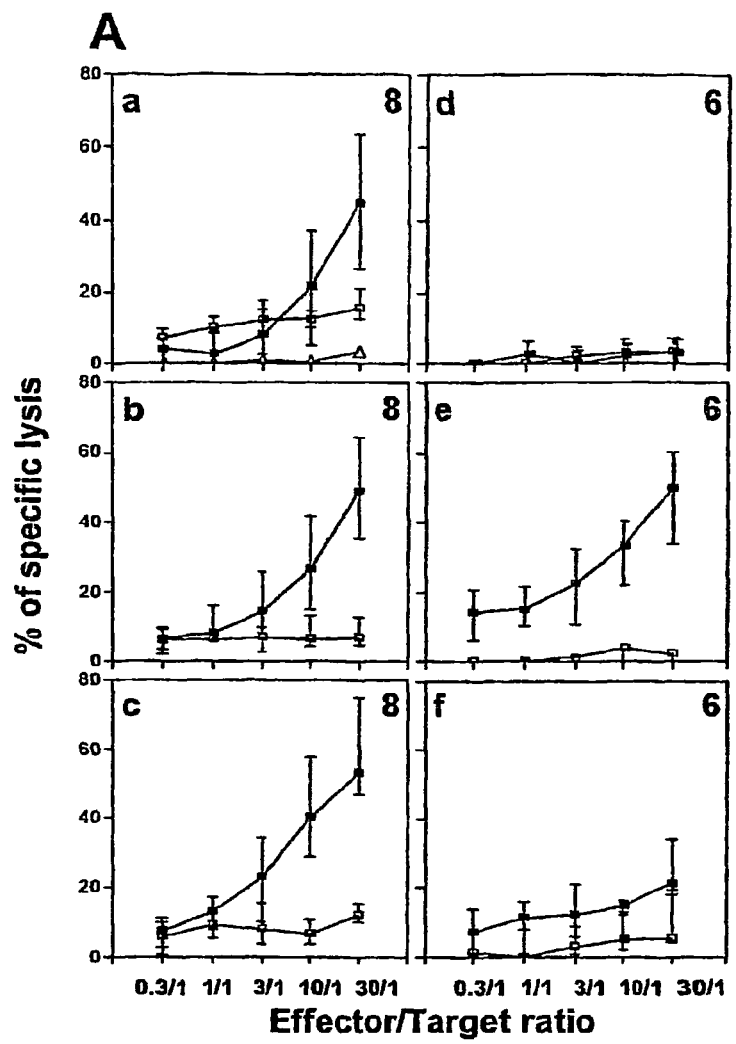
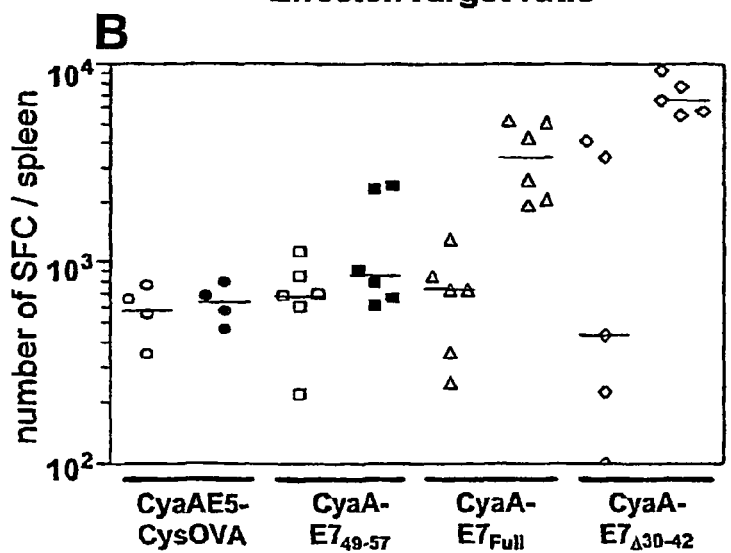

FIGURE 11
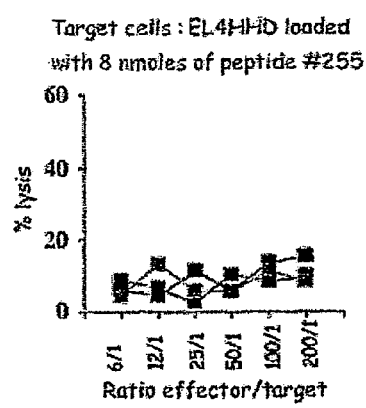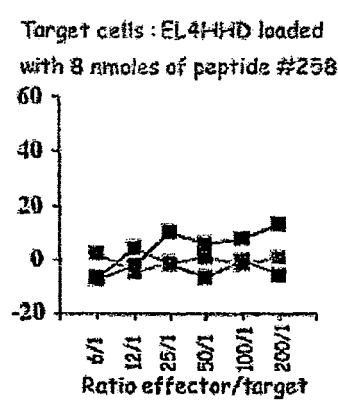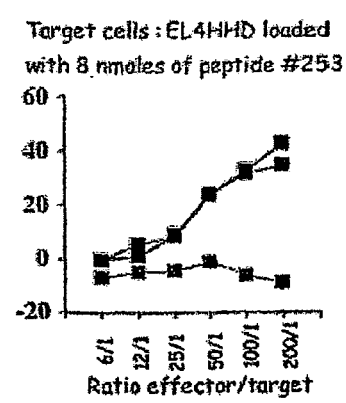

FIGURE 12
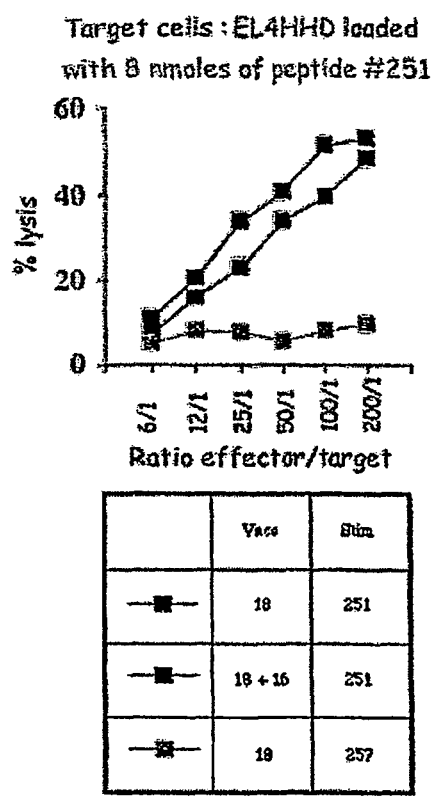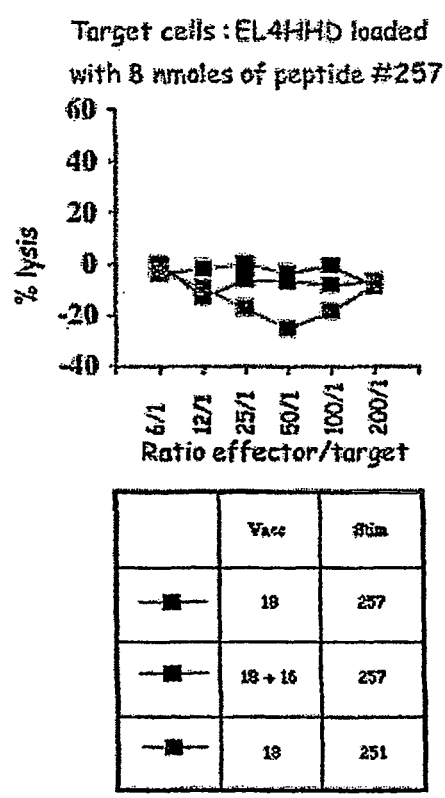

CONSTRUCTION of pTRACE5-E7HPV18
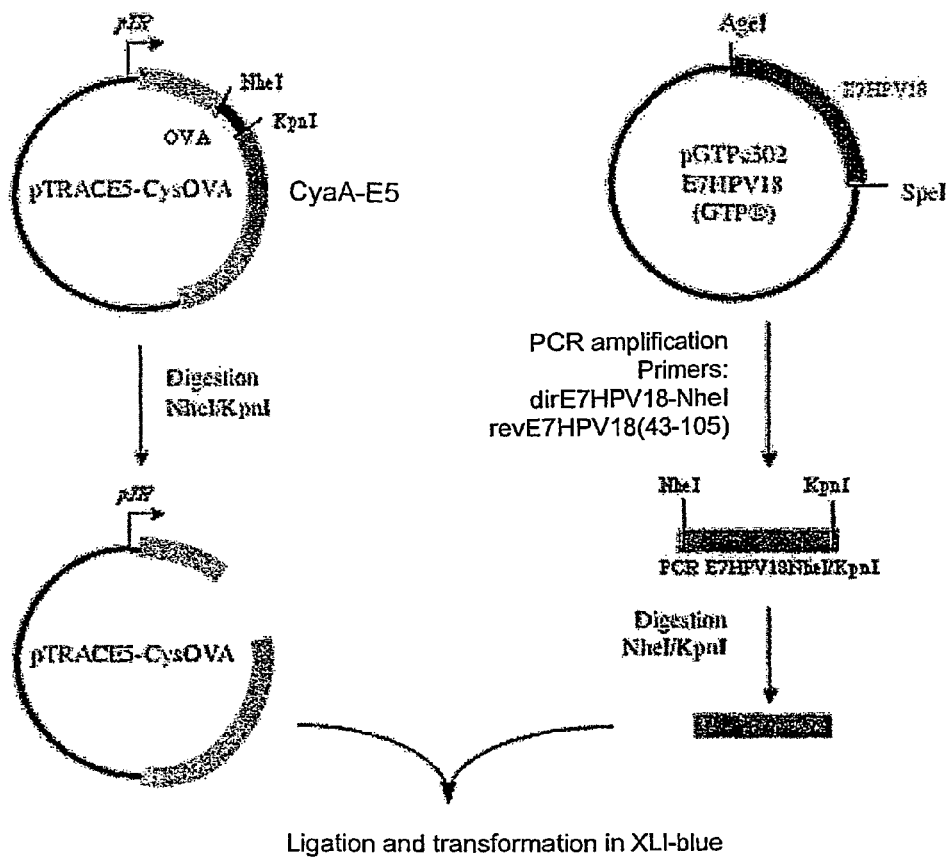
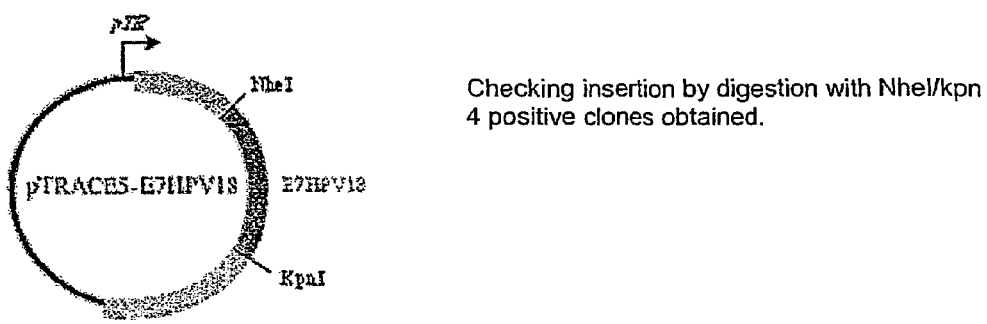
Checking insertion by digestion with NheI/kpn
4 positive clones obtained.
FIGURE 13

RECOMBINANT PROTEIN CARRYING HUMAN PAPILLOMAVIRUS EPITOPES INSERTED IN AN ADENYLATE CYCLASE PROTEIN OR FRAGMENT THEREOF. THERAPEUTIC USES THEREOF

CROSS REFERENCE TO RELATED APPLICATIONS

This application is a Continuation of PCT International Application No. PCT/EP2005/003452, filed on Mar. 18, 2005, the content of which is incorporated herein by reference, and claims the priority of European Patent Application No. 04290741.0, filed on Mar. 18, 2004, the content of both of which is incorporated herein by reference.

The present application relates to a recombinant protein carrying papillomavirus epitopes inserted in an adenylate cyclase protein or a fragment thereof.

Accordingly, the invention relates to recombinant proteins wherein the adenylate cyclase (CyaA) protein acts as a protein vector to elicit an immune response against epitopes derived from papillomavirus antigens especially human papillomavirus antigens.

The invention especially relates to the use of the proteinaceous vector thus obtained to deliver epitopes to eukaryotic cells, preferably to mammalian cells, and especially human cells.

The invention also concerns polynucleotides encoding the recombinant protein of the invention, together with vectors containing said polynucleotides as well as host cells containing said polynucleotides or vectors.

The invention also relates to applications of the above recombinant protein or polynucleotides for the treatment or prevention of human papillomavirus infection in a host as well as for the treatment or prevention of malignant effects resulting from infection, by human papillomaviruses, in a host, particularly in a mammalian host. In a particular embodiment, the invention provides means useful for the design of compounds suitable for immunotherapy, especially immunotherapy against tumor specific antigens of papillomaviruses.

Among the numerous human papillomavirus (HPV) types, those designated as high-risk HPVs are linked with the development of epithelial malignancies upon persistence of infection in the host (1). Cervical carcinoma, the second most widespread gynecological cancer worldwide (1), is associated (>99%) with the detection of mostly HPV16 and HPV18 DNA (2). The oncogenic potential of these viruses is attributed to the products expressed by early genes, i.e., E6 and E7 genes which expression is detected throughout the replication cycle of the virus and is necessary for the onset and the maintenance of malignant transformation. However, the high frequency of anogenital infection with these high-risk oncogenic HPV types (3) contrasts with the low proportion of individuals that will eventually develop HPV-associated malignancies, suggesting a control of high-risk HPV infections by immune responses. Several observations strengthened this statement such as the spontaneous regression of the majority of pre-malignant lesions (1), the infiltration of regressing genital warts by $CD4^+$ T cells and macrophages (1) as well as the higher number of infected subjects found in immunosuppressed or immunodeficient patients (1). Furthermore, $CD4^+$ and $CD8^+$ T-cell responses against HPV16-E6 and/or E7 epitopes were detected in the blood of patients diagnosed with HPV16-associated malignancies (4-8) as well as in the blood of healthy individuals (9, 10). Altogether, these considerations constituted a strong rationale for the development of immunotherapy targeting the E6 and/or E7 proteins of HPV16.

Many vaccine strategies have been developed to prevent tumor growth of HPV16-E6 and -E7-positive tumorigenic cell lines in C57BL/6 mice by generating immune responses to the $H-2D^b$ HPV16-$E7_{49-57}$-restricted epitope. These vaccination approaches have included plasmid DNA, viral or bacterial vectors, chimeric virus-like particles, synthetic peptides and recombinant proteins (11). Unfortunately, those approaches yielded mildly satisfying results in terms of clinical regression (3). Hence, it remains of interest to evaluate novel tools to target HPV-epitopes to immune system for induction of cellular mediated responses.

There is thus a need for new vectors suitable for delivering epitopes of HPV antigens to target cells, in conditions allowing the elicitation of a humoral and/or cellular-mediated immune response in a host against said antigens. The inventors have found that adenylate cyclase protein may be of interest in order to design such a vector. Various observations have been made, using adenylate cyclase protein of *Bordetella pertussis*, which led to the conclusion that this protein may represent a suitable basis for the design of such efficient vector.

The adenylate cyclase (CyaA) of *Bordetella pertussis* has the capacity to deliver its catalytic domain into the cytosol of eukaryotic cells (12). Thus, $CD4^+$ and $CD8^+$ T cell epitopes inserted into the catalytic site of CyaA are processed and presented by MHC class II and I molecules, respectively, at the surface of antigen-presenting cells (APC) (13). Furthermore, CyaA was recently demonstrated to bind specifically to the $\alpha_M\beta_2$ integrin (CD11b/CD18) (14, WO 02/22169) and so to target these T-cell epitopes to the $CD11b^+$ dendritic cell subpopulation (15). Immunization of mice with a recombinant CyaA bearing appropriate epitopes led to the induction of strong CTL responses, full protection against a lethal viral challenge and efficient prophylactic and therapeutic antitumor immunity (16, 17). The adenylate cyclase (CyaA) protein has been characterized and disclosed for its preparation by recombinant DNA technology especially in WO 93/21324 or WO 02/22169. In WO 02/22169, it has been described that fragments of CyaA encompassing residues 373 to 1706 contain the structure essentially required for interaction with the CD11b/CD18 receptor.

More specifically, it has been described later that the amino acid sequence extending from residue 1166 to amino acid residue 1281 comprise a determinant for interaction with the CD11b/CD18 receptor, and more particularly that amino sequence extending from residue 1208 to residue 1243 are critical for the interaction of the toxin with CD11b/CD18 (EP 03291486.3 and 45).

The inventors have now determined and evaluated conditions for the construction of a recombinant CyaA protein bearing, i.e., comprising, epitopes of HPV antigens, that can deliver said epitopes in target cells, especially in Antigen Presenting Cells (APC), of a host, including hosts suffering from HPV infection and from its malignant transformations.

Accordingly, the invention especially relates to a recombinant protein comprising one or several polypeptides bearing one or several epitopes of one or several HPV antigens, said polypeptides being inserted in the same or different permissive sites of an adenylate cyclase (CyaA) protein or of a fragment thereof wherein said CyaA fragment retains the property of said adenylate cyclase protein to target the target cells of CyaA such as APC, especially CD11b/CD18 cells, such as dendritic cells. In a particular embodiment, this fragment also retains the property of CyaA to allow translocation of the epitope inserted therein or of the polypeptide containing said epitope into the cytosol of a target cell. Translocation of the epitope or polypeptide containing said epitope into the cytosol of the target cell can be permitted if the fragment of CyaA retains the domain of the protein which permits translocation of its catalytic domain.

The recombinant protein of the invention can be prepared having recourse to recombinant technology. It can also be obtained by synthesis, especially by chemical synthesis. Hence, the terms "recombinant protein" refers to the chimeric form of the protein.

The capacity of the recombinant protein to target CD11b/CD18 cells can be assayed especially according to the methods disclosed in EP 03291486.3 and (45) or in WO 02/22169. Furthermore, the capacity of the recombinant protein to translocate the epitope or polypeptide containing said epitope into the cytosol of target cell can be assayed by applying the method described in WO 02/22169.

In a particular embodiment, the fragment of CyaA can be constituted of two different portions of CyaA which are not naturally contiguous in CyaA. As an example, one may cite the catalytic domain of CyaA, i.e., the 400 amino acid residues of the N-terminal part of CyaA and a fragment comprising amino acid residues 1208 to 1243 required for targeting of CD11b/CD18 Antigen Presenting Cells.

In the above definition, the expression "polypeptide" describes any amino acid sequence, including amino sequences undergoing post-translational modifications, especially amino acid sequence having at least six amino acid residues, and including amino-acid sequences having especially from 5 to 500 residues or from about 5 to about 100, or from about 5 to about 200 or from about 10 to about 50 residues, or from about 30 or about 50 to 200 residues, or from about 100 to about 210 or from about 100 to about 200 residues providing said amino acid sequence comprises at least one epitope, i.e., an amino acid sequence against which an immune response may be obtained after its delivery to a target cell, advantageously in a host, especially in a mammal host. Polypeptides according to this definition can thus be restricted to epitopes, even to a unique epitope or can comprise several different or identical epitopes or can also encompass full-length antigens from a pathogen, i.e., from human papillomavirus. Epitopes within the present invention encompass amino acid sequences which are involved in humoral immune response and/or cell-mediated immune response, especially in T cell immune response. Accordingly, epitopes in the polypeptides of the recombinant molecules of the invention include those which are processed by APC (Antigen Presenting Cells) in a host, especially those recognized in association with class I MHC (Major Histocompatibility Complex) molecules such as epitopes which target cells are CD8$^+$ T lymphocytes or epitopes recognized in association with class II MHC molecules such as those which target cells are CD4$^+$ T lymphocytes cells.

In a particular embodiment, the polypeptide bearing epitopes comprises several epitopes derived from different antigens, especially from one type of antigen of different HPV strains or from several types of antigens of different HPV strains. Hence, the polypeptide derived from HPV antigens can be multivalent, especially bivalent or trivalent, i.e., enabling an immune response against several antigens.

According to the present invention, HPV antigens from which the polypeptides bearing one or several epitopes can be designed, are preferably those derived from proteins especially involved in the onset and/or maintenance of malignant effects following HPV infection and encompass so-called tumor antigens, i.e., antigens associated with tumor development related to HPV infection, that can elicit an immune response in a host and react specifically with antibodies or T-cells in a host.

The polypeptides bearing epitopes according to the invention may be derived from native or mature antigens of HPV including by using the whole antigen or including by selecting fragments, especially antigenic fragments, especially epitopes of said antigens, rather than the whole protein or by modifying said antigen or its selected antigenic parts or epitopes, especially in order to improve their capacity to induce or elicit an immune response in a host when combined with CyaA protein in the recombinant molecule. Accordingly, to illustrate the various possible modifications of such epitopes, these polypeptides encompass epitopes which are flanked by naturally or non-naturally flanking sequences of the antigen from which they are derived, and also encompass epitopes or amino acid sequences containing epitopes which have been chemically modified in order to improve their immune properties. These modifications can be advantageous to improve the efficiency of the obtained polypeptides in the association with CyaA protein.

Some particular modifications are disclosed as examples hereafter, including modifications encompassing changes in the charge of the polypeptides, especially by insertion of additional positively-charged amino acid residues.

Accordingly, the polypeptide of the invention also encompasses semi-synthetic or synthetic polypeptide.

According to a particular embodiment, the polypeptides derived from HPV antigens contain, each or together, from about 5 to about 500, or from about 5 to about 100, or from about 5 to about 200, for example from about 10 to about 50 amino acid residues or from about 30 or about 50 to about 200 amino acid residues or from about 100 to about 210 or from about 100 to about 200 amino acid residues.

The polypeptide(s) is (are) chosen especially to enable elicitation of an antigen-specific response when recombined in the recombinant protein of the invention.

The recombinant protein of the invention can especially be designed to comprise a polypeptide or several polypeptides consisting in a disrupted native HPV antigen, wherein said disruption consists of a deletion of one or several amino acid residues in an acidic region of said HPV antigen, and/or an insertion of at least two polypeptide fragments of said HPV antigen in at least two permissive sites of the adenylate cyclase.

A particular disruption encompassed within this definition, is obtained by insertion of at least two fragments of the native HPV antigen, in at least two permissive sites of the adenylate cyclase, wherein these at least two fragments are reversed with respect to their natural location in the native antigen, i.e., the fragment which in the native antigen is more N-terminal becomes C-terminal when inserted in the CyaA protein or fragment thereof, and vice-versa.

It has been observed that the inversion of amino-terminal and carboxy-terminal fragments can be more effective in inducing strong and long-lasting protective immunity, especially in cancer immunotherapy, as illustrated with E7$_A$ fragments (i.e., fragments of the E7 antigen).

According to the invention, adenylate cyclase (CyaA) is used as a full-length protein or as a fragment thereof, as disclosed above.

Advantageously, the CyaA protein or a fragment thereof is a protein or a fragment thereof, which is the result of the co-expression in a cell, especially in a recombinant cell, of both cyaA and cyaC genes. It has been indeed shown that in order to have invasive properties for target cells, CyaA has to undergo post-translational modifications which are enabled by the expression of both cyaA and cyaC genes (WO 93/21324).

In a particular embodiment of the invention, fragments of the CyaA protein are fragments having at least about 30 amino acid residues and can have up to about 1300, in particular to about 500 amino acid residues, preferably from about 50 to about 150 amino acid residues; said fragments comprise, in a particular embodiment, amino acid residues 1166 to 1281 of CyaA or amino acid residues 1208 to 1243 of CyaA protein for interaction with CD11b/CD18 target cells. A particular fragment thus encompasses all or part of the C-terminal part of the native protein which part is responsible for the binding of the protein to target cell membrane and/or CD11b/CD18 receptor, and for the subsequent delivery of the epitope(s) contained in the polypeptide(s) into the cell cytosol (12). A particular fragment of CyaA protein according to the invention contains amino acid residues 372 to 1706 of CyaA protein. Another particular fragment is one which corresponds to the CyaA protein wherein amino acid residues 225 to 234 have been deleted, thus providing a CyaA fragment containing residues 1 to 224 and 235 to 1706.

In a particular embodiment of the invention, the adenylate cyclase protein is a bacterial protein. In a preferred embodiment, CyaA protein is derived from a *Bordetella* species.

Among *Bordetella* species of interest, according to the invention, one of them is *Bordetella pertussis*. Other *Bordetella* strains of interest are those of *Bordetella parapertussis* or *Bordetella bronchiseptica*. The sequences of CyaA protein of *B. parapertussis*, has been disclosed especially under accession number NC 002928.3 (as a sequence of 1740 amino acids) and in Parkhill J. et al (Nat. Genet. DOI, 10 (2003) and for *B. bronchiseptica* in Betsou F. et al (Gene 1995, Aug. 30; 162(1): 165-6).

*Bordetella pertussis* is the causative agent of whooping cough and secretes among others several toxins including the well-known pertussis toxin (PT) and the adenylate cyclase toxin (CyaA), which is a critical virulence factor of the bacterium and is one of the antigens protective against *B. pertussis* infection.

The adenylate cyclase protein of *Bordetella pertussis* is a toxin which has been described as a bifunctional protein of 1706 residues, comprising a N-terminal catalytic domain of 400 amino acid residues and a C-terminal part of 1306 residues which is responsible for the binding of the toxin to target cell membrane and subsequent delivery of the catalytic moiety into the cell cytosol (12).

The CyaA protein is synthesized as an inactive protoxin which is converted into an active toxin by post translational palmitoyation of two internal lysine residues (lysins 860 and 983). This post translational modification requires the expression with the cyaA gene of an accessory gene, i.e., cyaC which is located nearby cyaA on *B. pertussis* chromosome.

The cyaA of *Bordetella pertussis* has been described as an amino acid sequence and a nucleotide sequence by Glaser, P. et al, 1988, Molecular Microbiology 2(1), 19-30. Accordingly, when amino acid residues or sequences or nucleotides or nucleotide sequences of the CyaA protein of *B. pertussis*, are cited in the present invention their positions are given with respect to the sequences disclosed in said publication of Glasser et al. 1988.

In the recombinant protein according to the invention, the polypeptides bearing one or several epitopes of one or several HPV antigens, are inserted in one or several permissive sites of the CyaA protein.

For the present invention, a "permissive site" is a site of the sequence of the CyaA protein where a polypeptide can be inserted without substantially affecting the functional properties of the CyaA protein especially without substantially affecting the targeting of cells, particularly targeting of APC by CyaA, including without substantially affecting the specific binding to the CD11b-CD18 receptor and advantageously without substantially affecting the domains of the protein involved in the process of translocation of the epitope(s) into a target cell.

Permissive sites of the *Bordetella pertussis* adenylate cyclase allowing translocation of CyaA catalytic domain and hence translocation of epitopes inserted into such permissive sites include, but are not limited to, residues 137-138 (Val-Ala), residues 224-225 (Arg-Ala), residues 228-229 (Glu-Ala), residues 235-236 (Arg-Glu), and residues 317-318 (Ser-Ala) ((44) Sebo et al., 1995). The following additional permissive sites are also included in embodiments of the invention: residues 107-108 (Gly-His), residues 132-133 (Met-Ala), residues 232-233 (Gly-Leu), and 335-336 (Gly-Gln) and 336-337. (43)

For other *Bordetella* species corresponding permissive sites can be defined by comparison of sequences and determination of corresponding residues.

According to another embodiment, the polypeptide can also or alternatively be inserted at one and/or other extremities of CyaA protein or its fragment.

Particular fragments of CyaA proteins for use for the purpose of the invention are those comprising up to 1300 amino acids or from about 30 to about 500 amino acid residues, advantageously about 50 to about 150 amino acid residues in particular such fragments encompassing amino acid residues 1166 to 1281 of the native CyaA protein, advantageously 1208 to 1243 of native CyaA protein.

Thus, according to the invention, the "insertion" of a polypeptide in the CyaA protein to provide a so-called recombinant protein also referred to as a "hybrid protein", encompasses genetic insertion especially by available DNA technology. Alternatively, "insertion" also encompasses non genetic insertion, including chemical insertion for instance covalent coupling carried out at one extremity of the CyaA or fragment thereof, or non covalent coupling. Non-genetic insertion can especially be of interest when the polypeptide to be inserted is synthetic or semi-synthetic. Methods for coupling a drug to a polypeptide are well known in the Art and comprise for example disulfide linkage by using N-pyridyl sulfonyl-activated sulfhydryl.

In particular, it is possible to graft molecules especially comprising polypeptides of the invention to CyaA by a chemical linkage or by genetic insertion for in vivo targeting to target cells of Cya, such as ACP, for example CD11b/CD18 cells and particularly to the cytosol of said cells. Indeed, when coupling a molecule corresponding to a given CD8$^+$ T-cell epitope to the catalytic domain of detoxified CyaA, either by means of a disulfide bond or by genetic insertion, it has been found that the engineered molecule can elicit in vivo specific CTL response, thereby showing that said CD8$^+$ T-cell epitope is translocated into the cytosol of CD11b-expressing cells.

In a specific embodiment, the recombinant adenylcyclase used for the manufacturing of proteinaceous vector is a CyaA or fragment thereof especially modified by insertion of cysteine residues containing one or more molecule(s), especially comprising polypeptides of the invention, chemically coupled by means of a disulfide bond to genetically inserted cysteine residue(s) located within the catalytic domain of said adenylcyclase.

Indeed, multiple molecules especially comprising polypeptides of the invention, can be chemically coupled to the adenylcyclase by means of a disulfide bond to different cysteine residues located at different permissive sites within the catalytic domain.

With a view to propose a recombinant protein suitable for the design of products having the capacity to elicit an immune response, especially a cell-mediated immune response in a host, and in particular in order to design such products capable of eliciting an immune response against the malignant effects observed in a host infected with HPV, the inventors have proposed to derive polypeptides bearing epitopes from highly oncogenic HPV strains and especially from antigens from strains selected among HPV16, HPV18, HPV31, HPV33, HPV35, HPV45, HPV52 or HPV58.

Among these strains, HPV 18 and HPV 16 are of particular interest. HPV 16 is especially a particular target for treatment of a host infected with HPV, because of its association with the development of cervical cancer in mammal host especially in human.

Starting from these HPV strains, the inventors propose to derive polypeptides bearing epitopes from antigens selected among L1, L2, E1, E2, E4 and E5 proteins.

Alternatively or in combination, the inventors also propose to derive such polypeptides bearing epitopes from E6 or E7 proteins of HPV.

In a particular embodiment of the invention, E6 or E7 proteins of HPV16 or E6 or E7 proteins from HPV18 are used for the design of polypeptides bearing epitopes.

A particular HPV protein which can be referred to for the design of a polypeptide derived from HPV antigens is the E7 protein of HPV, especially of HPV16 or of HPV18. According to an embodiment of the invention, the polypeptide is derived from several E7 proteins of different HPV strains, especially of HPV16 and HPV18. For example, the polypeptide is the full length E7 protein of HPV 16 and HPV18 or one or several fragments of each of the E7 protein of HPV16 or HPV18, including multimers, especially dimers of said fragments.

These proteins of HPV and their amino acid and nucleotide sequences have been disclosed in Seedorf, K. et al (Human papillomavirus type 16 DNA sequence. Virology, 145: 181-185, 1985) for HPV16, Cole S. T., Danos O. (Nucleotide sequence and comparative analysis of the human papillomavirus type 18 genome. Phylogeny of papillomaviruses and repeated structure of the E6 and E7 gene products. J. Mol. Biol. 193: 599-606 (1987)) or in Fernando G J. et al (T-helper epitopes of the E7 transforming protein of cervical cancer associated human papillomavirus type 18 (HPV18) Virus Res. 1995 Apr. 36(1): 1-13).

The E6 and E7 proteins are oncoproteins expressed especially by HPV16 or HPV18 throughout the replicative cycle of the virus and they have shown to be necessary for the onset and maintenance of malignant transformation of host cells, following infection with HPV strain. Therefore, both these tumors specific antigens are considered as potential targets for adoptive CTL-mediated immunotherapy.

According to a particular embodiment of the invention, the recombinant protein comprises multiple polypeptides, each of them bearing one or several epitopes of one or several HPV antigens.

For example, such multiple polypeptides can be derived from E6 and E7 proteins of one HPV strain, especially from HPV16 or HPV18. According to another example, these multiple polypeptides can encompass epitopes derived from E6 or E7 proteins, from both HPV16 and HPV18.

Multiple polypeptides can also consist of different epitopes bearing fragments of one protein, for example of an E7 or E6 protein, which are inserted in different permissive sites of the CyaA protein of interest.

Another particular recombinant protein according to the above definitions is a protein CyaA recombinant wherein the multiple polypeptides bearing epitopes encompass a fragment comprising residues 1 to 29 or a fragment consisting of residues 1 to 29 or a fragment comprising residues 42 to 98 or a fragment consisting of residues 42 to 98 of E7 protein of HPV16, or multiple polypeptides comprising or consisting of both fragments, inserted in different permissive sites of the CyaA protein.

Another recombinant protein according to the invention is a protein wherein the multiple polypeptides encompass a fragment having amino acid sequence RAHYNIVTF (SEQ ID NO: 1) ($E7_{49-57}$) and/or GQAEPDRAHYNIVTFCCK-CDSTLRLCVQSTHVDIR (SEQ ID NO: 2) ($E7_{43-77}$).

It has been observed that the number of amino acid residues of the polypeptides inserted in permissive sites of the CyaA protein is such that it allows for polypeptides consisting of full-length antigens, especially of full-length E6 or E7 proteins of HPV to be inserted in CyaA protein or fragments thereof.

According to a particular embodiment of the invention, the polypeptide included in the recombinant CyaA is the E7 protein, especially the E7 protein of HPV16, inserted between codons 224 and 235 of CyaA or between codons 319 and 320 of CyaA.

In another embodiment, the recombinant protein of the invention comprises multiple polypeptides, some of which being polypeptides bearing an epitope or several epitopes of one or several HPV, and other polypeptides bearing epitopes of other pathogens.

In another particular embodiment, the recombinant protein of the invention further comprises one or several epitopes originating from a different pathogen agent. Association of epitopes originating from *Chlamydia* or from HIV retrovirus or HPV, HBV, HCV, adenoviruses EBV, herpes virus, HTLV.1 virus and CMV, with epitopes originating from HPV may especially be of interest.

According to another particular embodiment of the invention, the polypeptides bearing epitopes have been modified with respect to their native amino acid sequence, for example in order to decrease the number of negatively charged amino acid residues within the sequence. Such a modification can be obtained by removing some of these negatively charged amino acid residues or also by adding some positively charged amino acid residues, especially as flanking residues of the epitopes. Polypeptides thus comprising less negatively charged residues might favour the translocation of the catalytic domain of CyaA protein in the cytosol of target cells.

The polypeptides bearing epitopes can also be designed in such a way that they are unfolded when they are inserted in CyaA, which improve efficiency of the internalization of the recombinant CyaA protein into the target cells. Such unfolding in polypeptides which undergo folding as a consequence of their amino acid content, can be obtained for instance, by removing or substituting cystein residues in order to avoid formation of disulfide bonds that may be involved in folding of polypeptides. In some cases, it is possible to prevent folding of the polypeptides by preparing them in the presence of reducing agents to enable avoiding in vivo refolding.

In a particular embodiment, the polypeptides bearing epitopes can be cryptic epitopes.

In a particular aspect of the invention, the inventors have indeed determined that the chimeric protein constructs, made of the recombinant proteins which comprise (i) an adenylate cyclase (CyaA) or a fragment thereof according to the definitions disclosed above and (ii) a polypeptide bearing one or several antigenic fragments of one or several antigens, enable cryptic epitopes of said antigens to become immunogenic as a result of their presentation in the recombinant construct. Especially, said chimeric constructs involving CyaA or a fragment thereof as defined in the present invention and polypeptides derived from antigens of interest for especially therapeutic, including vaccinating, purposes can comprise cryptic epitopes of the antigen which are allowed to become immunogenic and in particular to raise a T-cell response in a host, especially a CTL response.

The invention thus also relates to a recombinant protein comprising one or several polypeptides bearing one or several epitopes of one or several antigens, said polypeptide(s) being inserted in the same or in different permissive sites of an adenylate cyclase (CyaA) protein or of a fragment thereof, said CyaA fragment retaining the property of said adenylate cyclase protein to target Antigen Presenting Cells, wherein at lease one of said epitope(s) is a subdominant cryptic T-cell epitope and wherein said recombinant protein is capable of eliciting an antigen-specific response against said polypeptide(s).

Especially, the cryptic epitopes are contained within an HPV antigen, in particular HPV16 and/or HPV18 antigens, especially an E7 antigen.

The recombinant protein thus defined especially comprises a peptide derived from HPV18 E7 protein, i.e., having amino acid sequence IDGVNHQHL (SEQ ID NO: 3).

According to a particular embodiment the cryptic epitope can be modified for example can have substitutions in the two first positions, and for instance can have sequence ASGVNHQHL (SEQ ID NO: 4).

The invention especially concerns peptides IDGVNHQHL (SEQ ID NO: 3).

The invention also concerns peptides having substitutions in this sequence, especially at positions 1 and/or 2, in particular peptides having sequence ASGVNHQHL (SEQ ID NO: 4).

The invention also comprises variants of said peptides, to the extent that they have immunogenic properties, especially capable of eliciting a T-cell, in particular a CTL response.

Advantageously, in order to prepare the recombinant protein of the invention, the enzymatic activity of the CyaA protein, i.e., its ability to convert ATP into cAMP, has been inactivated. Such inactivation may be obtained as a result of genetic inactivation. As an example, genetic inactivation can be obtained as a result of introduction of a dipeptide in a site of the amino acid sequence of CyaA which is part of the catalytic site (for example between 188 and 189). Such inactivated CyaA proteins are illustrated in the following examples.

The recombinant protein of the invention is advantageously capable of eliciting a cell-mediated immunoresponse. It includes CTL and Th, especially Th1 response, including $CD4^+$ T cell response and/or $CD8^+$ T cell response.

The ability of the recombinant protein to elicit this cell-mediated immune response has especially been shown to be sufficient to prevent tumor growth in vivo or even to enable tumor regression in an animal.

The invention also relates to a polynucleotide which encodes a recombinant protein as defined above.

A polynucleotide of the invention can be inserted in an expression vector to provide a recombinant expression vector suitable for expression of the recombinant protein of the invention. Such expression vectors include plasmids, cosmids, phagemids, viral vectors.

A recombinant vector can be one which is suitable for expression in prokaryotic cells, especially in bacteria or can be an expression vector suitable for expression in eukaryotic cells especially in mammalian cells, and advantageously in human cells.

The invention especially relates to vectors consisting of plasmids encoding a recombinant protein according to the invention such as: pTRACE5-HPV16E7$_{Full}$ (also designated CyaAE5-HPV16E7$_{FULL}$), deposited at the CNCM (Paris, France) COLLECTION NATIONALE DE CULTURES DE MICROORGANISMES (CNCM). 25 rue du Docteur Roux. F-75724 PARIS Cedex 15. FRANCE on Mar. 18, 2004 under number CNCM 1-3191; pTRACE5-HPV16E7$_{A30-42}$, (also designated CyaAE5-HPV16E7$_{A30-42}$), deposited at the CNCM (Paris, France) COLLECTION NATIONALE DE CULTURES DE MICROORGANISMES (CNCM). 25 rue du Docteur Roux. F-75724 PARIS Cedex 15. FRANCE on Mar. 18, 2004 under number CNCM 1-3190, or construct pTRACE5-HPV16E7$_{49-57}$.

The invention also comprises a host cell, especially prokaryotic cells, or eukaryotic cells, for example mammalian cells, including human cells, transformed with a polynucleotide or a vector according to the invention.

The invention especially relates to the host cells deposited at the CNCM under accession N° CNCM I-3190 and accession N° CNCM I-3191.

The invention also concerns an immunogenic composition which comprises as an active principle, a recombinant protein as defined above or a polynucleotide or an expression vector as defined above. Said active principle of the immunogenic composition can be formulated in association with a physiologically acceptable, vehicle, excipient, carrier or diluent or a combination thereof, suitable for administration to a host.

An immunogenic composition is advantageously designed to induce a cell-mediated immune response, in particular a T-cell mediated immune response, in a mammal host. Preferably, it is capable of inducing a cell-mediated cytolytic immune response CTL especially CD8+.

Another immunogenic composition according to the invention is one which can induce a humoral immune response.

In order to improve the capacity of the immune composition of the invention to induce an immune response, it may be interesting to combine the active principle with an adjuvant and/or a surfactant and/or immunomodulatory substances (such as cytokines or chemokines).

Adjuvant include, for example, liposomes, oily phases, such as Freund type adjuvents, generally used in the form of an emulsion with an aqueous phase or can comprise water-insoluble inorganic salts, such as aluminium hydroxide, zinc sulphate, colloidal iron hydroxide, calcium phosphate or calcium chloride.

The immunogenic composition according to the invention is advantageously used to induce an immune response in a host, either by priming and/or by boosting said response, especially for immunotherapy. Especially, an immunogenic composition of the invention can be of interest for prevention on the onset or maintenance of malignant transformation due to HPV infection in a host or for treatment of a patient suffering from malignant transformation due to HPV infection, especially HPV-16 or HPV-18 infection.

Such an immunotherapeutic composition may be of particular interest for therapy of uncontrolled cell proliferation in a host resulting in a tumorigenic state, especially for cancer immunotherapy in particular for cervical cancer immunotherapy associated with HPV infection. It therefore provides means for the design of therapeutic vaccines especially suitable for the treatment of malignant states due to oncovirus infections, including tumor states.

When used in the present invention, the expressions "treatment" or "therapeutic treatment" encompass the effects of the compounds disclosed in the present application, which result in a beneficial effect for the patient undergoing the treatment, said effects being either observed at a cellular level or at a clinical level, including encompassing, as a result of the treatment, an improvement of the condition of the patient or a remission state, or a recovery of a health state. When the malignant state treated is uncontrolled cell proliferation or tumor development or persistence, the beneficial effect can comprise the stabilization or preferably the prevention, stopping or reversal of uncontrolled proliferation or the regression of the tumor.

A composition intended for the treatment of a malignant state as described above can advantageously comprise a dose of active principle which can amount to from about 1 to about 1000 μg of recombinant protein, preferably from about 10 to about 500 μg of a recombinant protein. When the composition comprises as active principle a recombinant protein of the invention the dose can comprise from about 0.05 to about 10 μg of recombinant protein, preferably from about 0.1 to about 1 μg of protein.

Depending on the state to be treated, the composition can be administered locally at the level of the lesion, once or several times, for example at regular intervals of several days, for example, for 5 to 10 days. It can also be administered systemically.

The invention also relates to a vaccine composition, especially a composition formulated for administration to a mammal host, preferably to a human, comprising a recombinant protein according to the above definition or a polynucleotide as defined hereabove or a vector containing such polynucleotide, preferably in a human host, and if appropriate a pharmaceutically acceptable vehicle, for eliciting an immune response, including a cell-mediated immune response, and/or a humoral response.

The invention relates also to a drug composition comprising a recombinant protein or a polynucleotide or a vector of the invention, and a pharmaceutically acceptable vehicle, for preventing or treating HPV infections.

According to another embodiment, a drug composition comprises a recombinant protein according or a polynucleotide or a vector of the invention, with a pharmaceutically acceptable vehicle, for prevention or treatment of the onset or maintenance of malignant transformation due to HPV infection in a host.

A drug composition comprising a recombinant protein or a polynucleotide, or a vector and a pharmaceutically acceptable vehicle, for cancer immunotherapy.

The invention also concerns the use in a patient of recombinant proteins comprising a bacterial protein especially a bacterial toxin (preferably in their toxoid form) or a fragment thereof, suitable to be used as a vector to elicit an immune response, i.e., a humoral and/or a cell-mediated immune response in a host which protein or fragment thereof is modified by insertion of one or several epitopes of one or several antigens of one or several oncoviruses for the treatment of one oncovirus infection. Such a recombinant protein is proposed in particular for the treatment of malignant effects, especially tumors caused by infection by such oncovirus.

Examples of bacterial proteins suitable as vectors to carry epitopes of antigens of oncoviruses are OmpA from *klebsiella* or the following toxins Shiga toxin including its β subunit (Haicher N. et al J. Immunol. 2000, 165: 3301-8) Anthrax toxin (Goletz T J et al, PNAS USA 1997, 94: 12059-64), Diphtheria Toxin (Stenmark H. et al, J. Cell. Biol. 1991, 113: 1028-32) or *Pseudomonas* Exotoxin A (Donnelly J J. et al, PNAS USA 1993, 90: 9530-4). Oncoviruses which antigens can provide epitopes for preparing polypeptides for insertion in the bacterial protein includes HPV, HBV, HCV, adenoviruses EBV, herpes virus, HTLV.1 virus and CMV.

The description which is provided hereabove for the CyaA recombinant protein, uses as an active principal, could be adapted for other bacterial proteins and oncoviruses antigens.

The invention also relates to a kit for the diagnosis of an infection with an HPV or for immunomonitoring such infection, which comprises a recombinant protein, a polynucleotide or an expression vector according to the invention.

The invention also concerns the use of the above recombinant protein, polynucleotide or vector of the invention, for the treatment or for the prevention of HPV infection in a patient.

The invention also concerns the use of the above recombinant protein, polynucleotide or vector of the invention, for immunotherapy against the onset or maintenance of malignant transformation due to HPV infection in a patient.

The invention also relates to a method for the in vitro diagnosis or for the immunomonitoring of an infection with HPV, comprising:
  exposing T cells obtained from a mammal, especially from a human patient, to a recombinant protein of the invention,
  detecting a modification in the activation of T cells.

In a particular embodiment, the recombinant protein can be used for prevention of infection by HPV or for the treatment of hosts suffering from infection by HPV, including hosts harbouring tumor due to such infection.

The invention also relates to a process for the screening of unknown or sub-dominant cryptic T-cell epitopes in a polypeptide contained in a chimeric CyaA-polypeptide protein, wherein CyaA is the adenylate cyclase or a fragment thereof as disclosed above, which comprises:
  administering said chimeric protein to an animal host,
  determining the T-cell response of said host, especially the CTL response.

The invention especially relates to a process for screening unknown or sub-dominant or cryptic T-cell epitopes (especially $CD8^+$ T-cell epitopes) in the polypeptide(s) of HPV-antigen(s) contained in a recombinant protein defined within the invention, which process comprises:
  administering said recombinant protein to an animal host (non-human)
  determining the T-cell response of said host, especially the CTL response.

Further features characterizing the invention are disclosed and illustrated in the examples which follow and in the figures.

FIGURE LEGENDS

FIG. 1. Construction and purification of HPV16-E7 recombinant CyaAs.

(A) Schematic map of pTRACE5 in which relevant restriction sites and inserted sequences are indicated. (B) Schematic representation of CyaA showing the site of insertion of the dipeptide LQ to inhibit its enzymatic activity. Positions of the HPV16-E7 protein inserts are also shown. The HPV16-E7H-2b restricted epitope is underlined (SEQ ID NOS 23-26 are disclosed respectively in order of appearance). (C) SDS-Page analysis of the HPV16-E7 recombinant CyaAs. Five micrograms of the purified proteins were separated on a 4-15% SDS polyacrylamide gel and stained by Coomassie blue. Lane 1: wild-type CyaA; lane 2:CyaA-E7$_{49-57}$; lane 3: CyaA-E7$_{Full}$; lane 4:CyaA-E7$_{\Delta 30-42}$. (D) Western blot analysis of the HPV16-E7 recombinant CyaAs. Following SDS-PAGE, purified proteins were electro-transferred onto a nitrocellulose membrane that was subsequently probed with a mouse monoclonal anti HPV16-E7 antibody. Lane 1, 2: wild-type CyaA (2 and 0.4 µg, respectively); lane 3, 4 and 5: CyaA-E7$_{49-57}$,CyaA-E7$_{Full}$ and CyaA-E7$_{\Delta 30-42}$, respectively, 0.4 µg of each protein.

FIG. 2. Induction of T cell responses by recombinant HPV16-E7 CyaAs.

(A) C57BL/6 (a, b, c), TAP1$^{-/-}$ (d), MHC class II$^{-/-}$ (e) and CD40$^{-/-}$ (f) mice were immunized i.v. on day 0 with 50 µg of CyaA-E7$_{49-57}$ (a), CyaA-E7$_{Full}$; (b), or CyaA-E7$_{\Delta 30-42}$. (c, d, e and f). Seven days later, the animals were sacrificed, the splenocytes were restimulated in vitro for 5 days with 1 µg/ml of the HPV16-E7$_{43-77}$ peptide in the presence of irradiated syngeneic splenocytes, and used as effectors against TC-1 target cells (plain squares) or EL4 (open squares). Splenocytes from mice treated with CyaAE5-cysOVA carrying the non relevant epitope OVA$_{257-264}$ and restimulated in vitro for 5 days with 1 µg/ml of the HPV16-E7$_{43-77}$ peptide in the presence of irradiated syngeneic splenocytes are also represented (a, plain triangles). Target lysis was evaluated by $^{51}$Cr release. The data represent the median percentage of the specific lysis values (n=number of animals is indicated on each graph) as well as the interquartile ranges. (B) Detection of HPV16-E7-specific IFN-γ-producing cells after immunization with the recombinant HPV16-E7 CyaAs. C57BL/6 mice were immunized as in A with CyaAE5-cysOVA (circles), CyaA-E7$_{49-57}$ (squares), CyaA-E7$_{Full}$ (triangles), or CyaA-E7$_{\Delta 30-42}$ (diamonds). Seven days later, spleen cells isolated from immunized mice were cultured in vitro for 36 h without stimulation (i.e., no peptide, open symbols) or with 1 µg/ml of the E7$_{49-57}$ peptide (plain symbols) in the presence of syngeneic irradiated splenocytes. The data are expressed as the number of SFC per spleen and the result of individual mice of three independent experiments are represented for each group. Horizontal bars represent the median response of each group.

Figure 3:
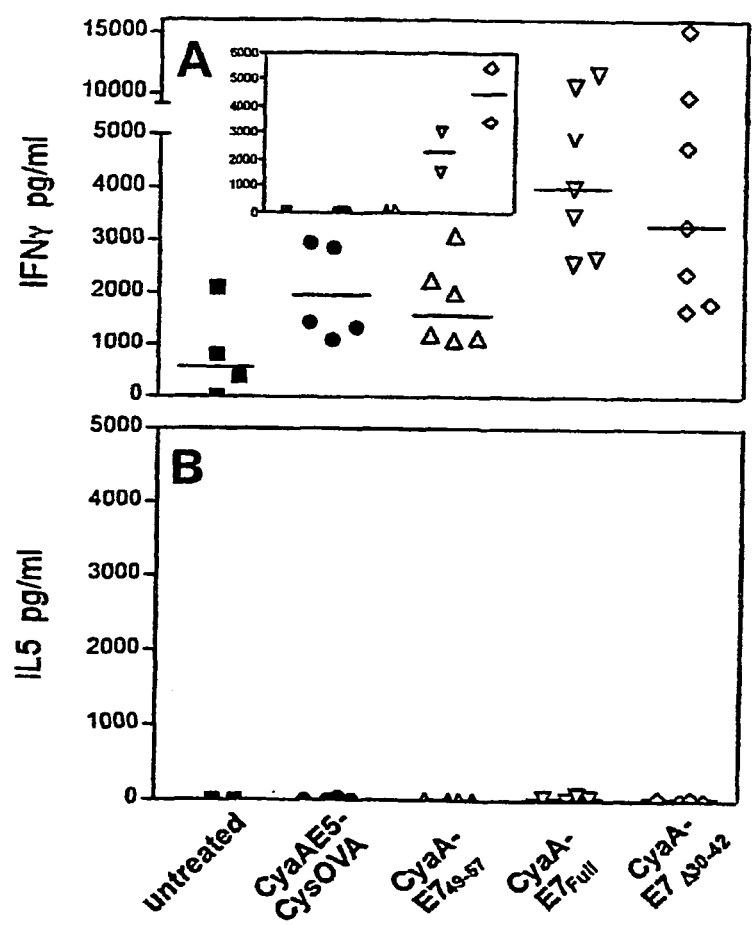

FIG. 3. Recombinant HPV16-E7 CyaAs induce a HPV16 E7-specific Th1 response.

(A) C57BL/6 mice were either left untreated (squares) or were primed i.v. with 50 µg of CyaAE5-cysOVA (circles), CyaA-E7$_{49-57}$ (triangles), CyaA-E7$_{Full}$ (inverted triangles), or CyaA-E7$_{\Delta 30-42}$ (diamonds). Seven days later, spleen cells were stimulated in vitro with 10 µg/ml of the His-Tag-HPV16-E7 protein, and the supernatants were tested for IFN-γ content 72 hours later. Results of individual mice of 4 independent experiments are represented and expressed as the concentration of IFN-γ released in the supernatant from duplicate wells. Backgrounds obtained with non restimulated splenocytes are subtracted. Inset: in vitro stimulation with 1 µg/ml E7$_{43-77}$ peptide. Horizontal bars represent the median response of each group. (B) Same as in (A) except that supernatants were tested for IL-5 content. Results of individual mice of 2 independent experiments are represented and expressed as the concentration of IL-5 released in the supernatant from duplicate wells.

Figure 4:
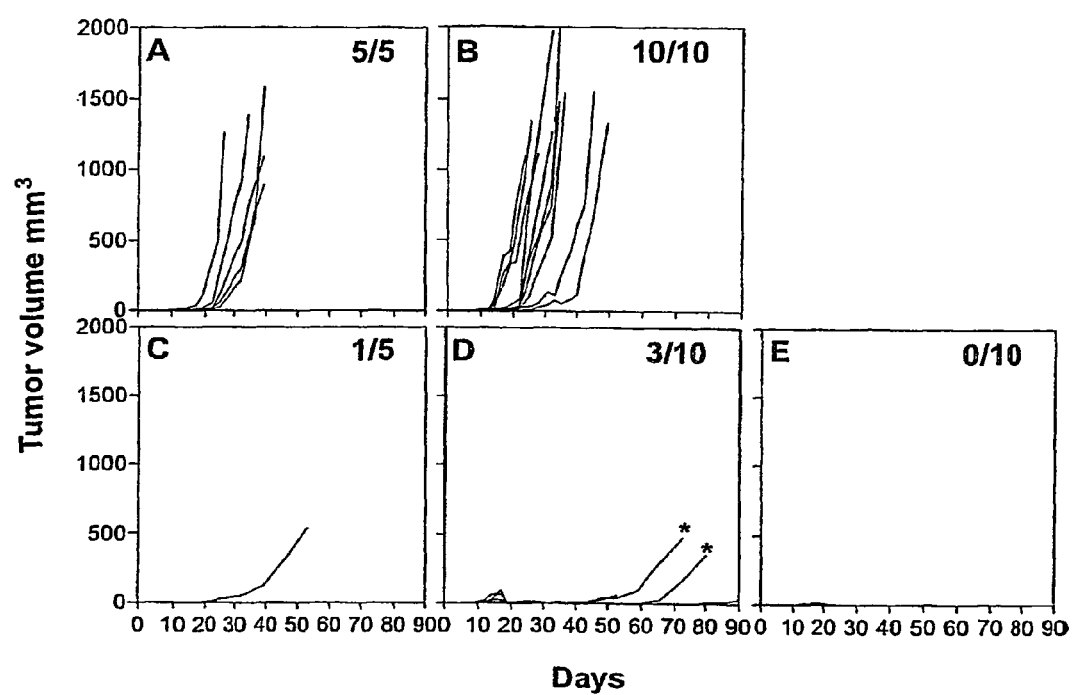
Figure 4:
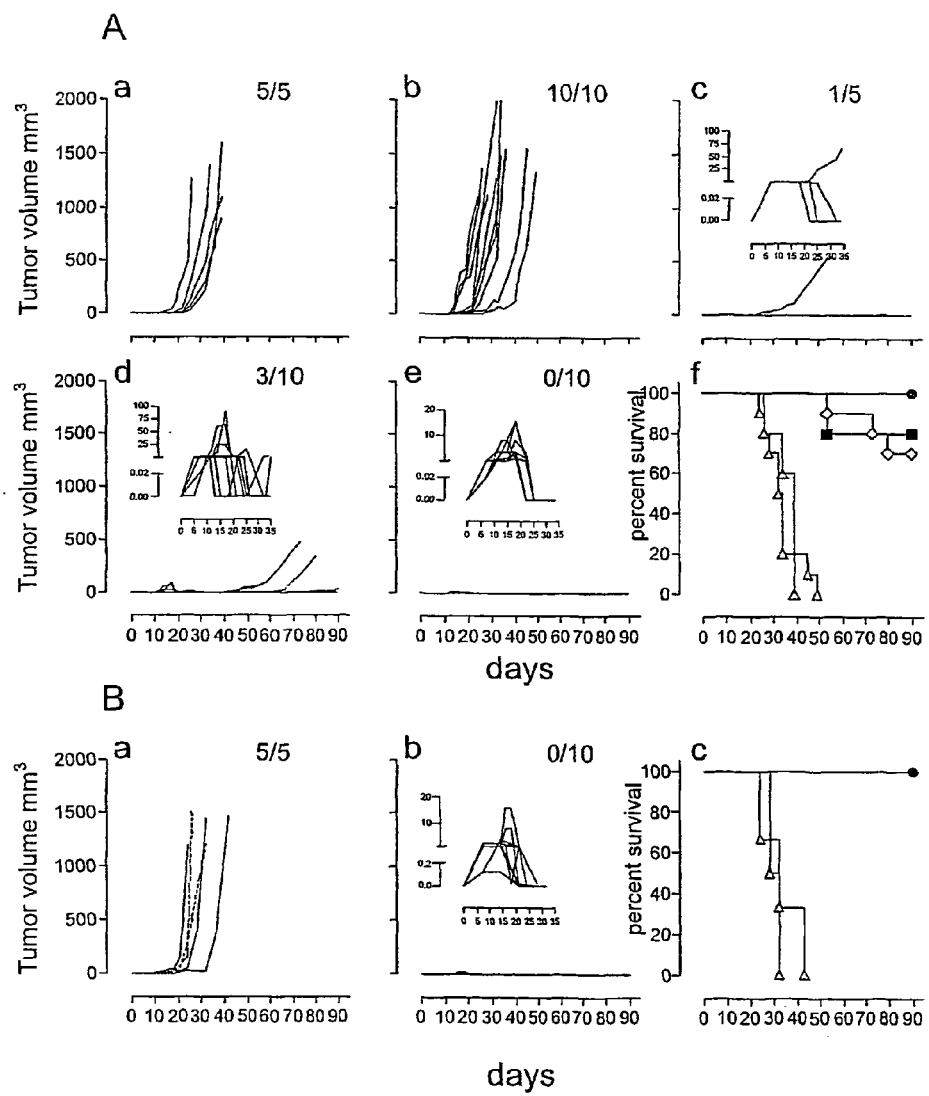

FIG. 4. Therapeutic vaccination with recombinant HPV16-E7 CyaAs eradicates established tumors.

(Exp. A) C57BL/6 mice were grafted on day 0 with 5×10$^4$ TC-1 tumor cells. On day 10, mice were treated with one i.v. injection of CyaA-E7$_{49-57}$ (C), CyaA-E7$_{Full}$ (D), or CyaA-E7$_{\Delta 30-42}$ (E). Mice left untreated (A) or injected with a CyaAE5-cysOVA (B) were taken along as controls. Mice were killed when the tumor size reached 1000 mm$^3$ or whenever the sanitary status of the animals commanded (necrosed tumor, rapid weight loss>20%) so as to avoid unnecessary suffering. Two mice treated with CyaA-E7$_{Full}$ that lately developed progressive tumors (*) were sacrificed for further investigation (see FIG. 6).

(Exp. B) Same as in (Exp. A) for the experimental setting. Therapeutic vaccination was performed in the ear dermis on days +10 and +17 with 10 µg of CyaAE5-CysOVA (a, solid lines) or 10 µg of CyaA-E7$_{\Delta 30-42}$ (b). Each curve represents the tumor growth in a single animal. Two untreated animals were included (a, dashed lines). In the top right of each quadrant (a, b) is indicated the number of sacrificed animals vs the total number of animals included. Survival curves of these mice are shown (c). Untreated (open triangles), mock-treated with CyaAE5-CysOVA (closed triangles), treated with CyaA-E7$_{\Delta 30-42}$ (circles).

Figure 5:
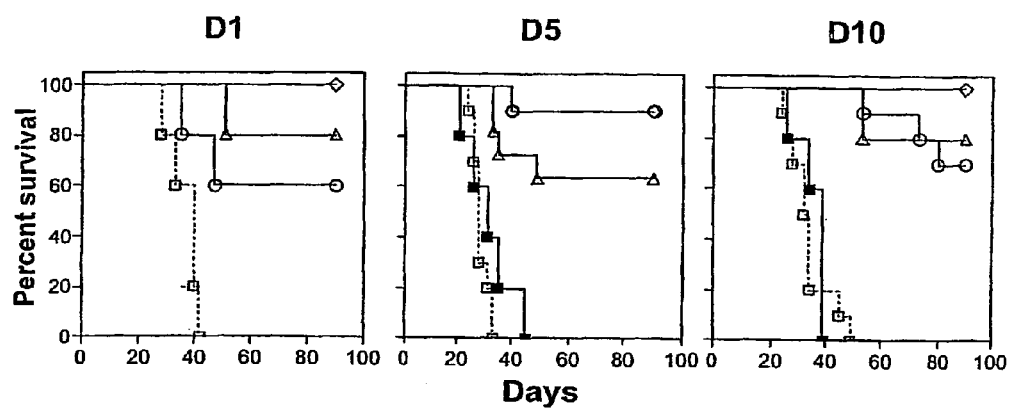

FIG. 5. Therapeutic vaccination with recombinant HPV16-E7 CyaAs results in prolonged survival. Therapeutic vaccination was carried out as described in FIG. 4. Upon injection with TC-1 tumor cells, mice (5 to 10 per group) were immunized with HPV16-E7 recombinant CyaAs at day +1, +5 or +10 as indicated on the graphs. Mice were left untreated (plain squares, solid line), mock-treated with CyaAE5-cysOVA (open squares, dashed line), or treated with CyaA-E7$_{49-57}$ (open triangles), CyaA-E7$_{Full}$ (open circles), or CyaA-E7$_{\Delta 30-42}$ (open diamonds). It is noted that in the day +5 therapeutic experiment, the survival curves of animals treated with CyaA-E7$_{Full}$ and CyaA-E7$_{\Delta 30-42}$ are completely superimposed. In every case, the survival of recombinant HPV16-E7 CyaAs-treated animals is significantly increased as compared to that of untreated or mock-treated mice (p<0.05).

Figure 6:
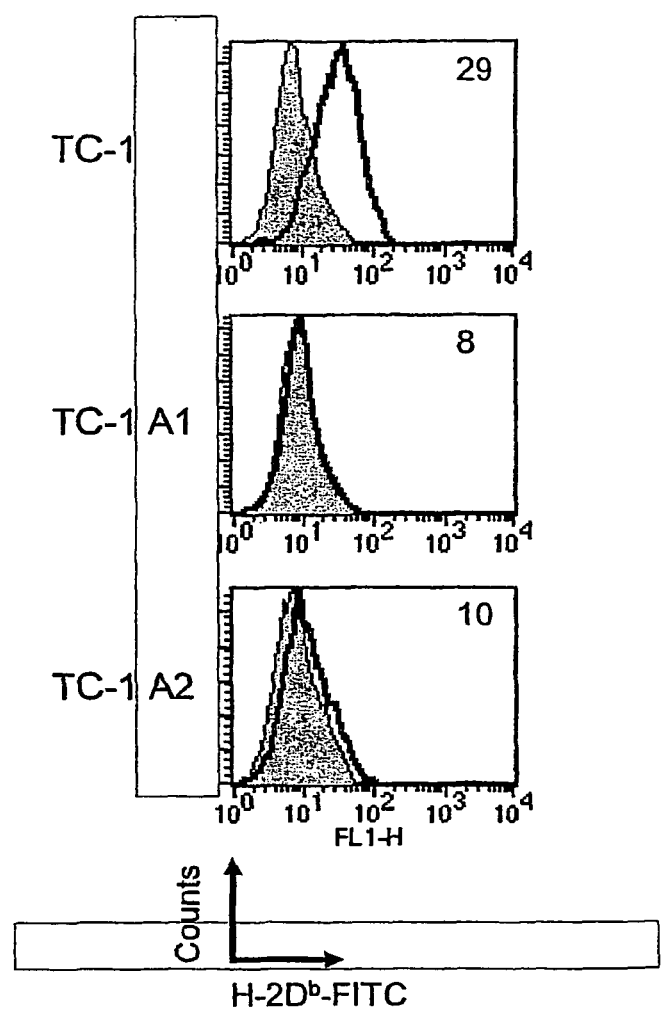

FIG. 6. TC-1 tumor cells explanted from lately growing tumors lose the expression of H-2D$^b$ molecule.

In tumor rejection experiments, some animals vaccinated with CyaA-E7$_{Full}$ grew tumors lately in the time course of the experiments (FIG. 4, *). Two animals were sacrificed to explant the tumors. These tumor cells, TC-1 A1 and A2 as well as native TC-1 cells were analyzed by FACS® for the level of expression of the H-2D$^b$ molecule (bold line). The medians of fluorescence intensities (MedFi) are indicated. Results obtained with isotype control are shown (gray shaded).

Figure 7:
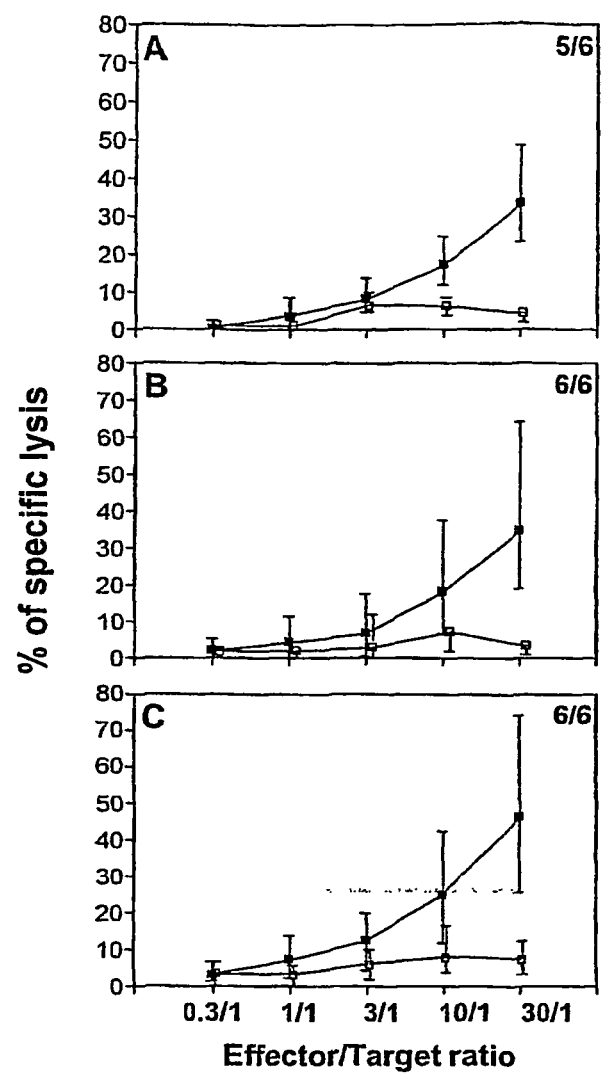

FIG. 7. Persistence of HPV16-E7$_{49-57}$ specific CD8$^+$ T-cells in mice treated with recombinant HPV16-E7 CyaAs.

C57BL/6 mice immunized with CyaA-E7$_{49-57}$ (A), CyaA-E7$_{Full}$ (B), or CyaA-E7$_{\Delta 30-42}$ (C) and surviving from TC-1 grafts in the therapeutic set of experiments were sacrificed and splenocytes were restimulated in vitro for 5 days with 1 µg/ml of the HPV16-E7$_{43-77}$ peptide in the presence of irradiated syngeneic splenocytes. Target lysis (TC-1, plain squares; EL4, open squares) was evaluated by $^{51}$Cr release. The data represent the median percentage of the specific lysis values (n=6 for each group) as well as the interquartile range. The number of responding animals, as determined by a specific lysis≥20% at the maximum effector to target ratio, is indicated in the upper right part of the quadrants.

Figure 8:
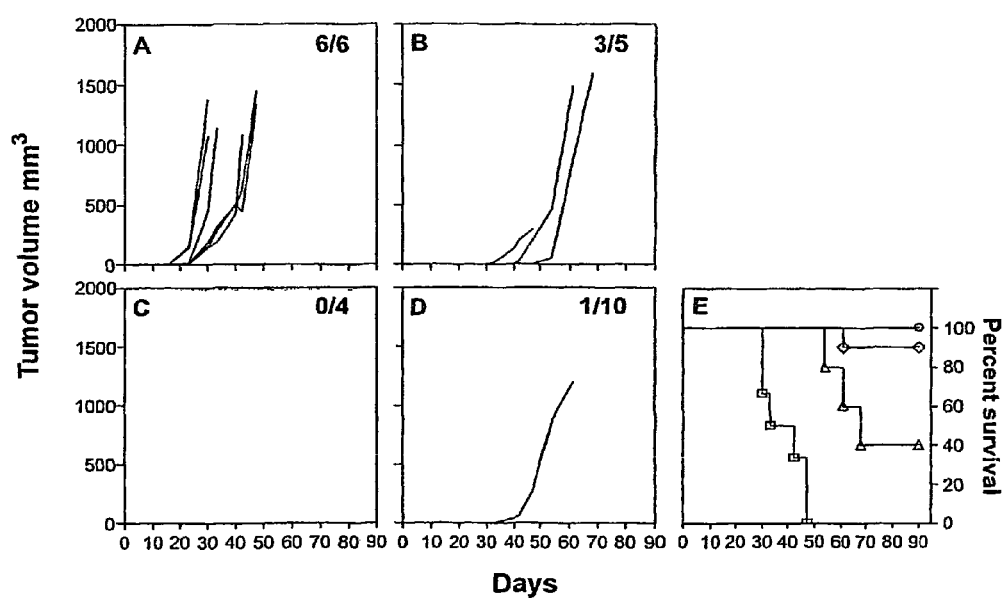

FIG. 8. Long term protection against TC-1 tumor growth induced by recombinant HPV16-E7 CyaAs.

Surviving C57BL/6 mice from TC-1 grafts in the therapeutic set of experiments were re-grafted s.c. at day 100 with 5×10$^4$ TC-1 cells. Age-matched untreated mice were taken along as controls (A). Growth of tumors in mice initially immunized with CyaA-E7$_{49-57}$, CyaA-E7$_{Full}$, and CyaA-E7$_{\Delta 30-42}$ are represented (B, C and D, respectively). Mice were killed when the tumor size reached 1000 mm$^3$ or whenever the sanitary status of the animals commanded. (E) Survival curves of animals (untreated, open squares; or immunized with Cya-E7$_{49-57}$, open triangles; CyaA-E7$_{Full}$, open circles; or CyaA-E7$_{\Delta30-42}$, (open diamonds) and regrafted with TC-1 cells (day of graft taken as 0). In every case, the survival of recombinant HPV16-E7 CyaAs-treated animals is significantly increased as compared to that of untreated or mock-treated mice ($p<0.05$).

Figure 9:
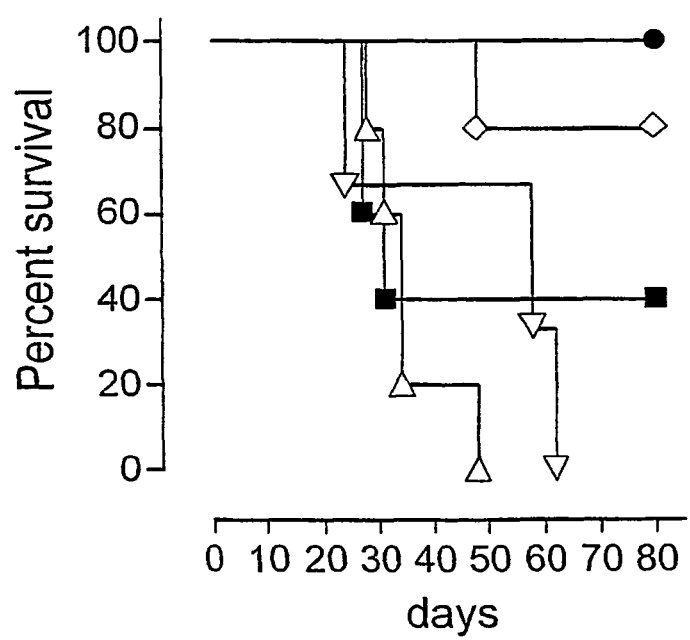

FIG. 9. Comparison of CyaA-E7$_{\Delta30-42}$ therapeutic activity to that of CpG ODN 1826-adjuvanted HPV16E7$_{43-77}$.

C57BL/6 mice were grafted s.c. on day 0 with $5\times10^4$ TC-1 tumor cells. Mice were treated on days +10 and +17, with one i.d. injection of 10 µg HPV16-E7$_{43-77}$ (n=5, triangles), 1 µg CpG-ODN 1826 (n=5, squares), 10 µg HPV16-E7$_{43-77}$+1 µg CpG-ODN 1826 (n=5, diamonds), 10 µg CyaA-CysOVA (n=3, inverted triangles), or 10 µg CyaA-E7$_{\Delta30-42}$ (n=7, circles). Mice were killed when the tumor sizes were above 1000 mm$^3$ or whenever the sanitary status of the animals commanded.

Figure 10:
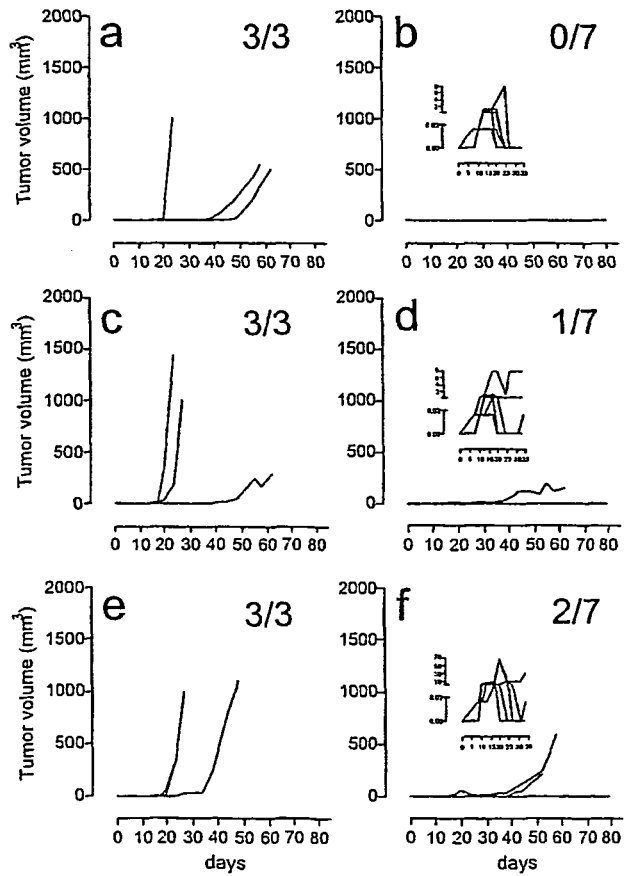

FIG. 10. Analysis of the effect of pre-immunity to CyaA on the ability of CyaA-E7$_{\Delta30-42}$ to induce TC-1 tumor rejection.

(A) C57BL/6 mice were either left untreated or immunized at day −90 or day −30, with two injections i.d. at a 7-days interval of 10 µg of CyaAE5. At day −1, animals were bled and sera were individually assessed by ELISA for the presence of anti-CyaAE5 IgGs. Results are expressed as individual antibody titers calculated by linear regression analysis plotting dilution versus A$_{492}$. Horizontal bars represent the median response of each group. (B) Untreated (a, b), day −30 CyaAE5-immunized (c, d), and day −90 CyaAE5-immunized (e, f animals were grafted s.c. on day 0 with $5\times10^4$ TC-1 tumor cells and were treated on days +10 and +17, with one i.d. injection of 10 µg CyaA-cysOVA (a, c, e), or 10 µg CyaA-E7$_{\Delta30-42}$ (b, d, f). Insets (b, d, f) are close-ups of the 0-35 days period to show that all animals had palpable tumors at the time vaccination was given. Each curve represents the tumor growth in a single animal. Mice were killed when the tumor sizes were above 1000 mm$^3$ or whenever the sanitary status of the animals commanded. In the top right of each quadrant is indicated the number of sacrificed animals vs the total number of animals included.

FIG. 11. Induction of CTL responses in HHD mice by CyaA-HPV16E7$_{\Delta30-42}$.

The peptide loading of EL4-HHD cells is indicated above each graph. In the tables below are indicated the type of CyaA injected (related to HPV16E7 or HPV18E7) under the column header Vacc and the peptide used for in vitro restimulation under the column header Stim. As one can see, following CyaA-HPV16E7$_{\Delta30-42}$ immunization, we were able to induce CTL specific for peptide #253 only (right panel). This CTL activity was specific since in vitro restimulated splenocytes with peptide #255 were not cytotoxic towards peptide #253-coated EL4-HHD cells (right panel). The absence of CTL-specific responses towards the two others HLA-A2 restricted peptide may result from different phenomenons: (i) the immunodominance of peptide #253, (ii) the absence of processing of peptides #255 and #258 by the proteasome of EL4-HHD cells, (iii) the poor solubility of peptide #258 for which we had to use acetonitrile (50%) that may be toxic for the cells. Most interestingly, co-injection of CyaA-HPV18E7$_{\Delta32-42}$ did not interfere with the CTL inducing ability of CyaA-HPV16E7$_{\Delta30-42}$ (right panel).

FIG. 12. Induction of CTL responses in HHD mice by CyaA-HPV18E7$_{\Delta32-42}$.

The peptide loading of EL4-HHD cells is indicated above each graph. In the tables below are indicated the type of CyaA injected (related to HPV16E7 or HPV18E7) under the column header Vacc and the peptide used for in vitro restimulation under the column header Stim. As one can see, following CyaA-HPV18E7$_{\Delta32-42}$ immunization, we were able to induce CTL specific for peptide #251 only (left panel). This CTL activity was specific since in vitro restimulated splenocytes with peptide #257 were not cytotoxic towards peptide #251-coated EL4-HHD cells (left panel). As for HPV16E7 HLA-A2 restricted peptides, the absence of CTL-specific responses towards HPV18E7 #257 HLA-A2 restricted peptide may result from different phenomenons: (i) the immunodominance of peptide #251, (ii) the absence of processing of peptide #257 by the proteasome of EL4-HHD cells, (iii) the poor solubility of peptide #257 for which we had to use acetonitrile (50%) that may be toxic for the cells. Most interestingly, co-injection of CyaA-HPV16E7$_{\Delta30-42}$ did not interfere with the CTL inducing ability of CyaA-HPV18E7$_{\Delta32-42}$ (left panel).

FIG. 13. Construction pTRACE5-E7HPV18

Figure 14A:
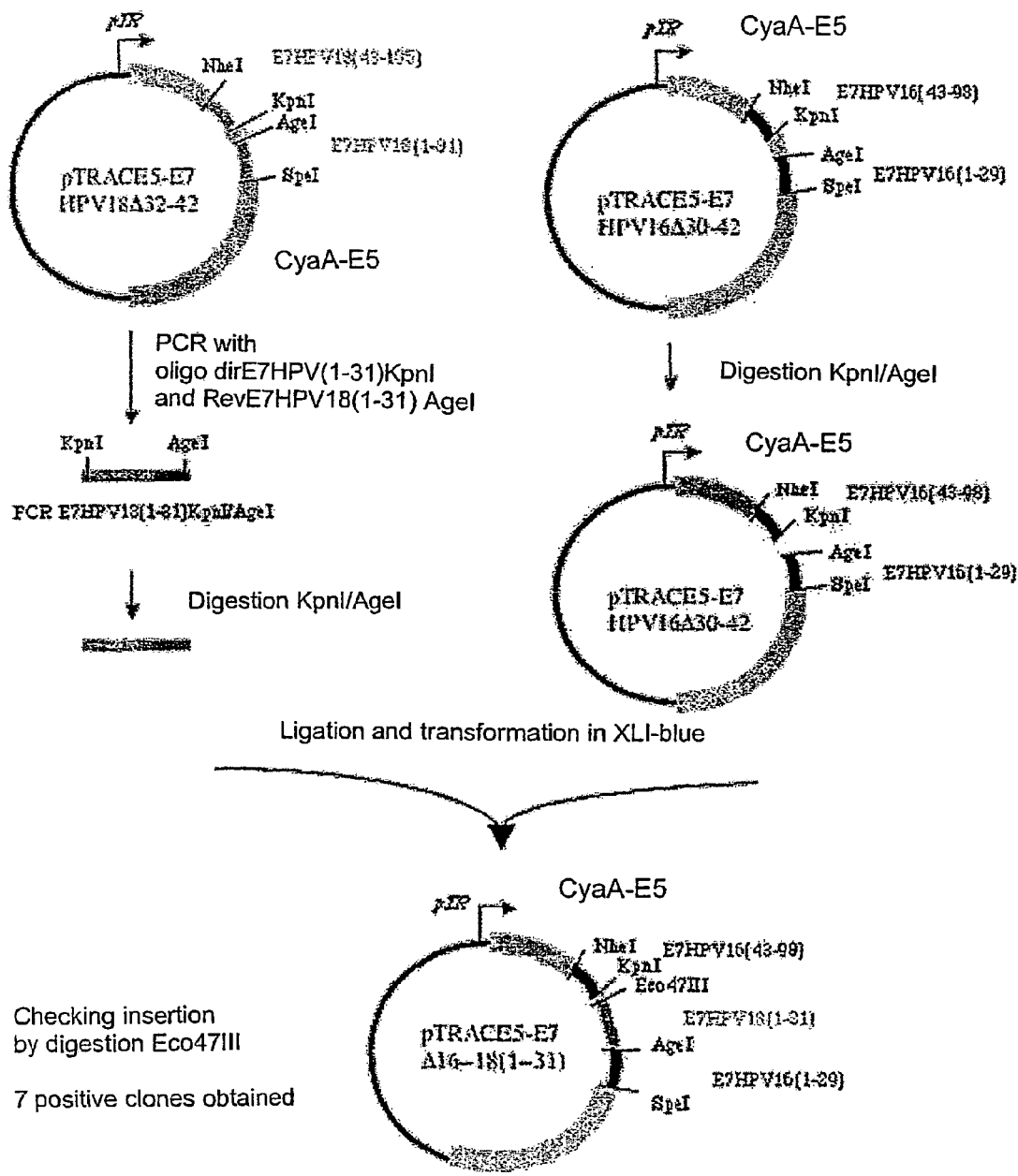
Figure 14B:
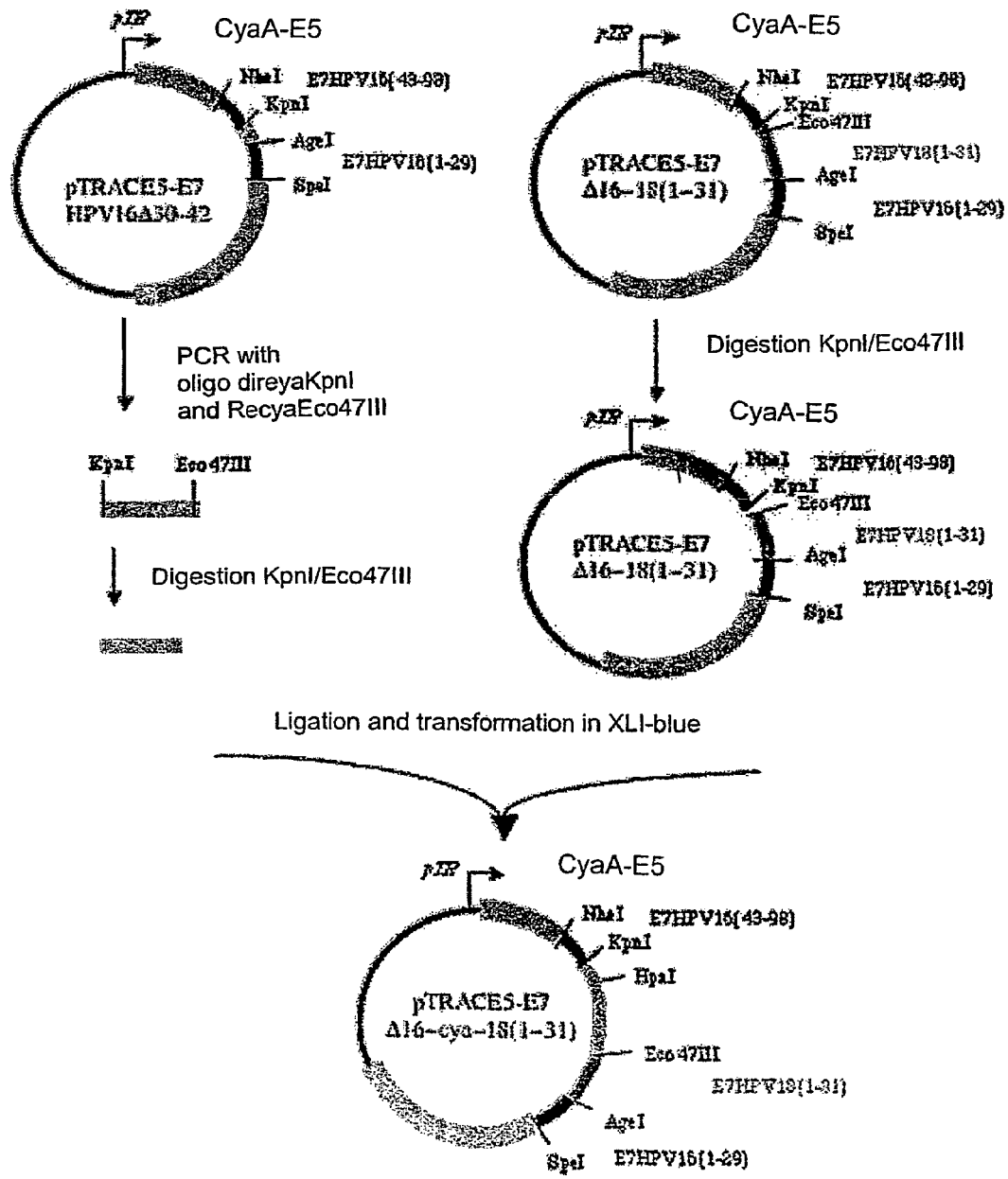
Figure 14C:
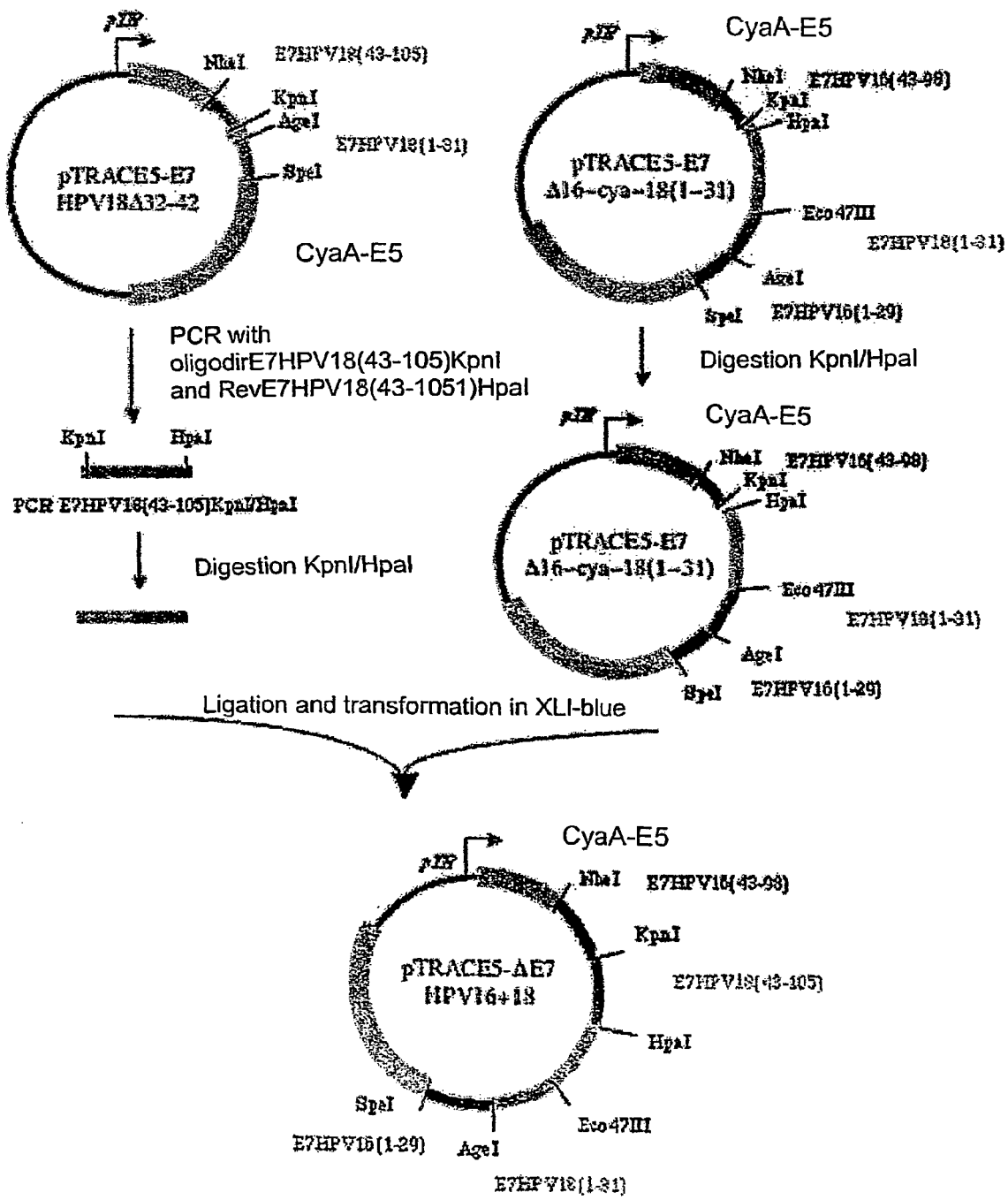

FIG. 14. Construction pTRACE5-E7ΔHPV16+18

3 steps for plasmid preparation are disclosed.

Figure 15:
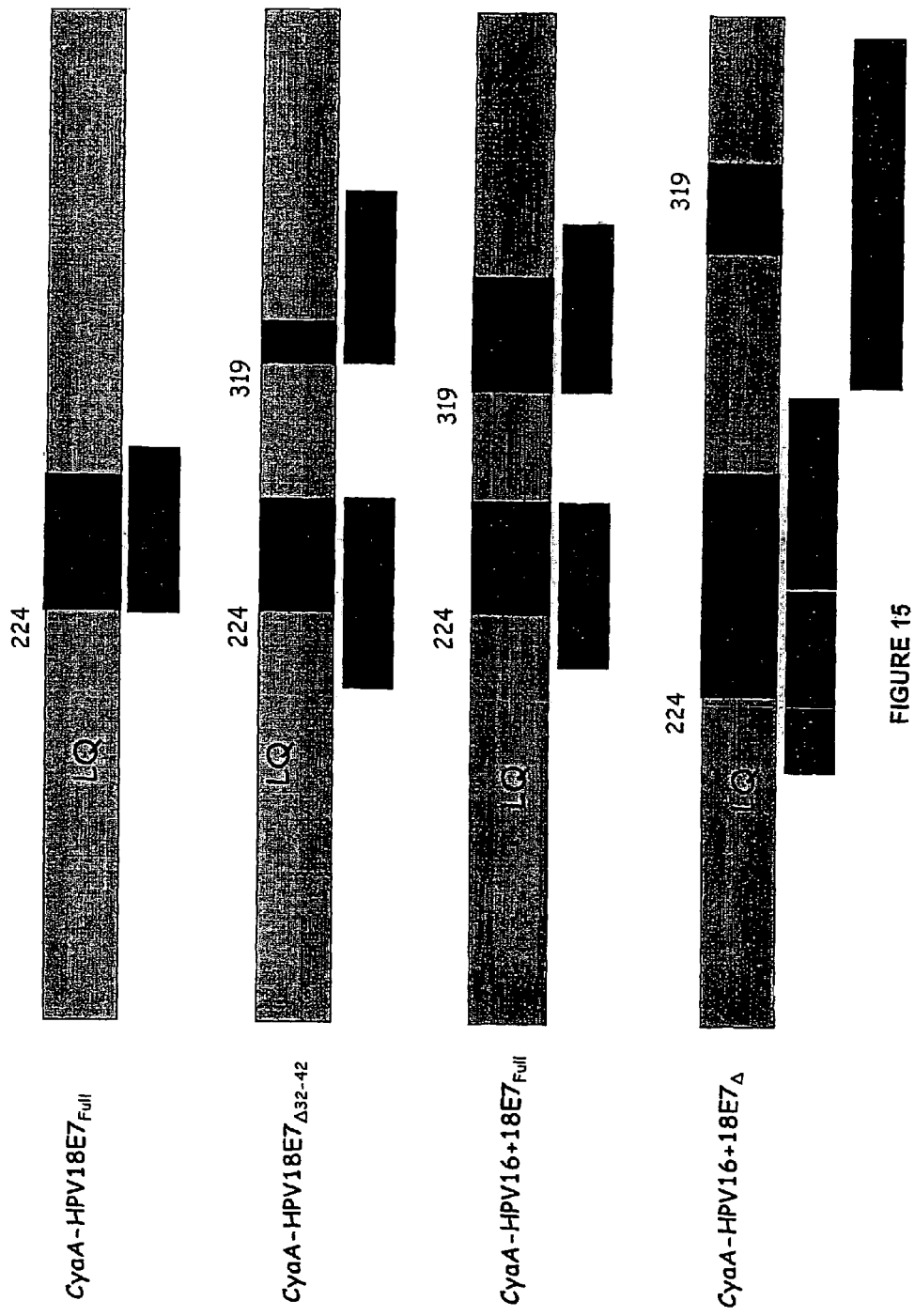

FIG. 15: Map of polynucleotide encoding:
CyaA-HPV18E7$_{Full}$
CyaA-HPV18E7$_{\Delta32-42}$
CyaA-HPV16+18E7$_{Full}$
CyaA-HPV16+18E7$_{\Delta}$ FIG. 16: Induction of CTL by recombinant CyaAs carrying HPV18E7 in C57BL/6 mice.

Figure 17:
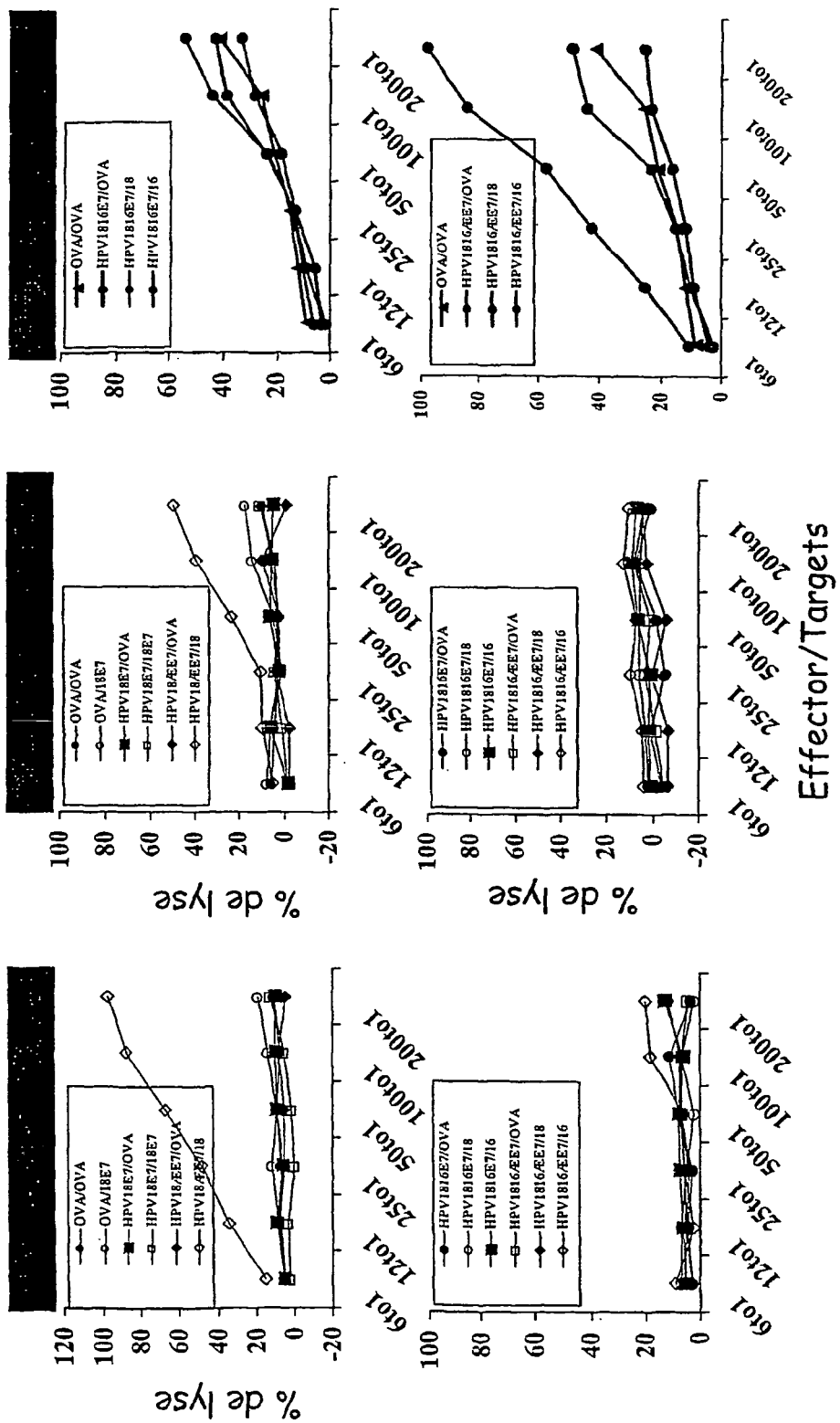

FIG. 17: Induction of CTL by recombinant CyaAs carrying HPV18E7 in C57BL/6 mice.

The deposited material (I-3190 and I-3191) is contained in *E. coli* strain BLR and can be grown in Luria Broth (LB) medium, and seeded in LB with 100 µg/ml Ampicillin, and can be incubated at 30° C., in air with shaking at 175 rpm and illumination. Conservation overnight is possible with LB in 7-10% DMSO.

EXAMPLES

Example 1

Here, we constructed recombinant CyaA containing either the full-length sequence of the E7 protein from HPV16 or subfragments of this polypeptide (in particular, a peptide encompassing residues 49-57 of E7 that corresponds to a H-2D$^b$ restricted epitope and HPV16-E7 residues 43-98 plus 1-29). We showed that, when injected to C57BL/6 mice, these HPV16-E7-recombinant CyaAs are able to induce specific CTL and Th1 responses characterized by the secretion of IFN-γ. Furthermore, when tested therapeutically, these constructions were able to provide up to 100% protection against the subcutaneous graft of TC-1 cells. This study represents the first demonstration of the in vivo anti-tumoral therapeutic activity mediated by CyaA against human tumor specific antigens.

Materials and Methods

Mice and Cell Lines.

Specific pathogen free 6-10-week old female C57BL/6 mice were obtained from CER Janvier (Le Gesnet St-Isle, France) or Charles River (L'Arbresle, France). TAP1$^{-/-}$ (18), MHC Class II$^{-/-}$ (19) and CD40$^{-/-}$ (20) bred onto a C57BL/6 background were also used in this study. Animals were kept in the Pasteur Institute animal facilities under pathogen-free conditions with water and food ad libitum. Experiments involving animals were conducted according to the institutional guidelines for animal care.

TC-1 cells expressing HPV16 E6 and E7 proteins (21) and mouse thymoma EL4 cells (17) were obtained from ATCC. Cells were maintained in RPMI 1640 with Glutamax supplemented with 10% heat-inactivated FCS, 100 U/ml penicillin, 100 µg/ml streptomycin, 0.4 mg/ml geneticin (for TC-1 cells only) and $5.10^{-5}$ M 2-mercaptoethanol (Gibco BRL, Cergy-Pontoise, France).

Peptides.

The synthetic peptidesE749 57 (RAHYNIVTF (SEQ ID NO: 1), one-letter code for amino acid) corresponding to the HPV16-E7H2-$D^b$-restricted epitope (22) and $E7_{43-77}$ (GQAEPDRAHYNIVTFCCKCDSTLRLCVQSTHVDIR; SEQ ID NO: 2) corresponding to the $E7_{49-57}$ CTL epitope with its natural flanking sequence and a Th epitope (bold) (23) were purchased from Neosystem (Strasbourg, France). CpG ODN 1826 was purchased from PROLIGO (Paris, France).

Construction and Purification of Recombinant B. pertussis Adenylate Cyclase Carrying HPV16-E7 Epitopes.

Recombinant adenylate cyclase used in this article were expressed in E. coli by using derivatives of plasmid pTRACE5 (FIG. 1A) which codes for an enzymatically inactive CyaA (24) (25). Plasmid pTRACE5 is an expression vector for an enzymatically inactive, and therefore cytotoxic, variant of B. pertussis CyaA. It also expresses B. pertussis CyaC protein that is required for the postranslational acylation of CyaA. This plasmid is a derivative of the previously described pTRACG plasmid (Gmira et al., 2001, Res. Mic. 152:889). It was obtained by insertion of the hexanucleotide CTGCAG in the EcoRV site located within the 5' part of the cyaA DNA sequence. This results in an in-frame insertion of the dipeptide Leu-Gln between Asp188 and Ile189 of CyaA within an essential part of the catalytic site (Guermonprez et al. 2000, Meth. Enzymol. 326:527).

Plasmid pTRACE5 harbors a ColE1 origin of replication and an Ampicillin resistant marker. In this plasmid, the cyaC and the modified cyaA genes are placed in the same transcriptional unit under the control of the λ phage Pr promoter. The pTRCAG plasmid also encodes the thermosensitive λ repressor $cl^{857}$ that strongly represses gene transcription at the λ Pr promoter at temperatures below 32° C.

The E. coli strain XL1-Blue (Stratagene, La Jolla, Calif.) was used for all DNA manipulations that were performed according to standard protocols (Maniatis et al.).

CyaA-$E7_{49-57}$ contains a 9-amino acid long polypeptide sequence (RAHYNIVTF; SEQ ID NO: 1) inserted between codons 224 and 235 of CyaA. The expression plasmid for CyaA-$E7_{49-57}$ was constructed as follows. Two synthetic oligonucleotides (MWG, Courtaboeuf, France), BTP1 (5'-CTA GCC GTG CCC ATT ACA ATA TTG TAA CCT TTG GTA C-3' coding strand (SEQ ID NO: 5)) and BTP2 (5'-CAA AGG TTA CAA TAT TGT AAT GGG CAC GG-3' non coding strand (SEQ ID NO: 6)) were annealed and ligated into the pTRACE5 digested with NheI and KpnI. CyaA-$E7_{Full}$ contains the entire sequence of the HPV16-E7 protein, i.e., 98 amino acids, inserted at the same 224 position of the enzymatically inactive CyaA. The DNA sequence encoding the E7 protein was amplified from HPV16 DNA (Seedorf K et al above) using specific primers BTP3, (5'-GGG CGC TAG CAT GCA TGG AGA TAC ACC TAC-3'; SEQ ID NO: 7), and BTP4 (5'-GGG CGG TAC CTG GTT TCT GAGAAC AGA TGG G-3'; SEQ ID NO: 8). The resulting PCR product was digested by NheI and KpnI and ligated into pTRACE5 cleaved by NheI and KpnI. The SspI site present in the annealed oligonucleotide as well as in the full sequence of HPV16-E7 allowed rapid identification of insertion mutants. CyaA-$E7_{\Delta 30-42}$ contains the first 29 amino acid residues of HPV16-E7 inserted between codons 319 and 320 of CyaA as well as residues 43 to 98 of HPV16-E7 inserted between codons 224 and 235 of CyaA. The expression plasmid for CyaA-$E7_{\Delta 30-42}$ was constructed in two steps. A first DNA fragment encoding (amino acid residues 1 to 29) of HPV16-E7 was PCR amplified using as a target DNA a synthetic HPV16-E7 gene (optimized for production in E. coli, designed by GTP Technology, Labege, France), and primers BTP5 (5'-GGG CAC CGG TAA ACG TAT GCA CGG CGA TAC TCC G-3'; SEQ ID NO: 9), and BTP6 (5'-CGT GAG CAT CTG GCT TTC ACT AGT ACG TTT GTT CAG CTG CTC GTA GCA-3'; SEQ ID NO: 10). A second DNA fragment encoding codons 320 to 372 of CyaA was PCR amplified using pTRACE5 as target DNA and primers BTP7 (5'-GGG CAC TAG TGA AAG CCA GAT GCT CAC GCG CGG G-3'; SEQ ID NO: 11), and BTP8 (5'-AGT ACA TCC GGC GAG AAC-3'; SEQ ID NO: 12). These two DNA fragments (that partly overlap) were purified and combined with primers BTP5 and BTP8 in a third PCR to amplify a 294 by long DNA fragment. This fragment was digested by AgeI and BstBI and inserted between the corresponding sites of pTRACE5 to yield plasmid pTRACE5-$E7_{1-29}$. Then, a DNA fragment encoding the amino acid residues 43 to 98 of HPV16-E7 was PCR amplified using the synthetic HPV16-E7 gene as target DNA and primers BTP9 (5'-GGG CGC TAG CGG TCA AGC AGA ACC GGA C-3'; SEQ ID NO: 13) and BTP10 (5'-GGG CGG TAC CAG GTT TTT GAG AGC AAA TCG GACAAA CAA TCC CCA GAG TAC CCA TC-3'; SEQ ID NO: 14). The purified PCR fragment was digested by NheI and KpnI and ligated into plasmid pTRACE5-E7129 digested by the same restriction enzymes.

All recombinant adenylate cyclase were produced in the Escherichia coli strain BLR (Novagen, Madison, Wis.) as described previously (26). The recombinant proteins were purified close to homogeneity (FIG. 1B) from inclusion bodies by a two-step procedure that includes DEAE-Sepharose and phenyl-Sepharose chromatography, as described previously (26). An additional washing step with 60% isopropanol in 20 mM Hepes-Na, pH7.5, was added to the phenyl-Sepharose chromatography in order to eliminate most of the contaminating LPS. LPS contents were determined using the kit QCL-1000 (Biowhittaker, Walkersville, Md.). Purified recombinant proteins were analyzed by SDS-gel analysis. Protein concentrations were determined spectrophotometrically from the absorption at 280 nm using a molecular extinction coefficient of 142,000 $M^{-1}.cm^{-1}$.

Construction and Purification of Recombinant HPV16-E7 Protein.

The E. coli-optimized cDNA coding for HPV16-E7 protein (GTP technology) DNA sequence available upon request was sub-cloned in pIVEX2.4b vector (Roche Molecular Biochemicals, Meylan, France) between NcoI and XhoI restrictions sites. The resulting plasmid was then transformed into the E. coli strain BL21λXDE3 (Novagen). The His-Tag-HPV16-E7 protein was expressed upon induction with 0.5 mM isopropyl-β-D-thiogalactopyranoside (Euromedex, Souffelweyersheim, France) and purified on Ni-NTA agarose (Qiagen, Hilden, Germany) according to the manufacturer's instructions. Isopropanol washes were used as described in (27) in order to remove LPS contamination.

Immunoblotting.

Proteins were separated by SDS-PAGE and electrotransferred to a nitrocellulose membrane (0.45µ, BioRad, Marnes la Coquette, France) that was probed with a mouse monoclonal anti HPV16 E7 antibody (Zymed, San Francisco, Calif.) or with a polyclonal anti E. coli BLR serum prepared in C57BL/6 mice. Immune complexes were detected with goat anti-mouse immunoglobulins conjugated to phosphatase alkaline (Chemicon, Temecula, Calif.) and revealed with 5-bromo-4-chloro-3-indolylphosphate/nitroblue tetrazolium (BCIP/NBT) (Sigma, St. Louis, Mo.).

Mice Immunization and Tumor Rejection Experiments.

Animals were immunized with one intravenous injection of 50 µg, or with two intradermal injections (10 µg each) of control or HPV16-E7 recombinant CyaAs diluted in PBS (Gibco BRL) Intradermal injections were performed in the ear dermis (47). For in vitro analysis, euthanazied animals ($CO_2$) were splenectomized 7 days after the injection except for the analysis of long lasting responses for which this procedure was carried out 3 months after the injection. For tumor rejection experiments, mice received $5 \times 10^4$ TC-1 cells subcutaneously and were treated by HPV16-E7 recombinant CyaAs 1 day, 5 days or 10 days after tumor inoculation. TC-1 Tumor growth was monitored using a caliper and expressed in cubic millimeters using the formula $V=(L \times w^2)/2$ (L: length, w: width) (48).

In Vitro Cytotoxic Assay.

Splenocytes from immunized mice were stimulated in vitro with 1 µg/ml of either $E7_{49-57}$ or $E7_{43-77}$ peptides in the presence of syngeneic irradiated naive spleen cells in complete medium (RPMI 1640 with Glutamax supplemented with 10% heat-inactivated FCS, 100 U/ml penicillin, 100 µg/ml streptomycin and $5.10^{-5}$ M 2-mercaptoethanol) during 5 days. The cytotoxic activity of these effector cells was tested in a 5-h $^{51}$Cr-release assay on TC-1 cells. Radiolabeling was performed as follows: exponentially growing TC-1 cells cultured in a 7.5% $CO_2$ atmosphere at 37° C. were quickly trypsinized (Trypsin-EDTA, GibcoBRL) and incubated with 100 µCi of $^{51}$Cr for 1 h at 37° C. Various E:T ratios were used and all assays were performed in duplicate. The radioactivity released in the supernatant of each well was measured. The percentage of specific lysis was calculated as 100×(experimental release−spontaneous release)/(maximum release−spontaneous release). Maximum release was obtained by adding 10% Triton X405 to target cells and spontaneous release was obtained with target cells incubated in complete medium alone. Mice are considered as responders when at least 20% specific lysis was observed at the highest E:T ratio. Results are expressed as medians±interquartile ranges of responder mice per group.

Single IFN-γ Producing Cell Enzyme-Linked-Immunospot Assay for Secreting Cells.

Multiscreen filtration plates (96 wells; Millipore, Molshein, France) were coated with 4 µg of rat anti-mouse gamma interferon (IFN-γ) antibody (clone R4-6A2; PharMingen, San Diego, Calif.) per ml, overnight at room temperature. Then the plates were washed and blocked with complete medium. Serial two-fold dilutions of spleen cells from immunized mice were added to the wells along with $5 \times 10^5$ γ-irradiated (2,500 rads) syngeneic feeder cells. The cells were incubated for 36 h with or without $E7_{49-57}$ peptide at 1 µg/ml. After extensive washes, the plates were revealed by incubation with 5 µg of biotinylated rat anti-mouse IFN-γ antibody (clone XMG 1.2; PharMingen) per ml followed by incubation with streptavidin-alkaline phosphatase (PharMingen). Finally, spots were revealed using BCIP/NBT as the substrate. The number of IFN-γ-producing cells was determined by counting the number of spot-forming cells (SFC) in each well (Bioreader, Karben, Germany), and the results were expressed as the total number of SFC per spleen (17).

Enzyme-Linked Immunosorbent Assay (ELISA).

Mice immunized intradermally with empty vector CyaAE5 were bled 30 or 90 days later and individual mouse sera were tested for antibody responses by ELISA. Microplates (Nunc, Roskilde, Denmark) were coated overnight with empty vector CyaAE5 (3 µg/ml) in PBS. After washes in PBS-tween 20 (0.1%), diluted sera were added to the wells and incubated for 1 hour at 37° C. Following washes in PBS-tween 20, plates were incubated with goat anti-mouse IgG peroxidase conjugate (Sigma) for 1 hour at 37° C. Plates were developed using o-phenylenediamine and hydrogen peroxide (Sigma). The reaction was stopped with sulfuric acid and the plates analyzed at 492 nm in an ELISA reader (Dynatech, Marnes la Coquette, France). Results are expressed as antibody titers calculated by linear regression analysis plotting dilution versus $A_{492}$. The titers were calculated to be the $\log_{10}$ highest dilution that gives twice the absorbance of pooled control sera diluted 1/100.

Cytokine Production.

Spleen cells from immunized mice were stimulated in vitro with 10 µg/ml of HisTag-HPV16-E7 protein or 1 µg/ml $E7_{43-77}$ peptide in complete medium for 72 hours. IFN-γ and IL-5 production was determined in culture supernatants by sandwich enzyme-linked immunosorbent assay (ELISA) as previously described (28). All assays were standardized with corresponding recombinant murine cytokines (Pharmingen).

FACS® Analysis.

TC-1 cells were processed as described elsewhere (29) for the analysis by flow cytometry of the level of expression of the MHC class I molecule H-2 $D^b$ using a specific FITC-conjugated monoclonal antibody (clone KH95, Pharmingen, Le Pont de Claix, France).

Statistical Analysis.

Considering the small size of the different samples, non parametric statistical tests (30) were applied using the software StatXact 4 (Cytel corporation, Cambridge, Mass.). Survival curves were plotted using Prism software (GraphPad Software Inc., Calif.) and compared with the software's built-in logrank test. Data were considered significantly different at $p<0.05$.

Results

Construction and Characterization of Recombinant Adenylate Cyclases Bearing HPV16-E7 Epitopes.

To study the ability of CyaA to induce HPV16-E7 specific T cell responses, we constructed 3 different recombinant molecules. CyaA-$E7_{49-57}$ contains a 9-amino acid long polypeptide sequence (RAHYNIVTF; SEQ ID NO: 1) corresponding to the previously described H-2$D^b$ restricted CTL epitope (22), that was inserted between codons 224 and 235 of an enzymatically inactive (hence nontoxic) CyaA. CyaA-$E7_{Full}$ contains the entire sequence (98 amino acids) of the HPV16-E7 protein inserted at the same 224 position of the enzymatically inactive CyaA CyaA-$E7_{A30-42}$ contains the first 29 amino acid residues of HPV16-E7 inserted between codons 319 and 320 of the enzymatically inactive CyaA as well as residues 43 to 98 of HPV16-E7 inserted between codons 224 and 235. To allow in vitro and in vivo assays, the CyaA constructs were produced and purified close to homogeneity (FIG. 1B) An LPS elimination procedure was introduced in the purification protocol (26) to obtain recombinant proteins containing less than 100 units of endotoxin per 50 µg. The presence of the E7 protein in CyaA-$E7_{Full}$ and CyaA-$E7_{A30-42}$ was confirmed by western blotting using a specific monoclonal antibody (Zymed) (FIG. 1C). In contrast, CyaA-$E7_{49-57}$ containing only the H-2$D^b$ restricted epitope was not recognized by the anti-HPV16-E7 antibody. The overall biochemical properties of the 3 recombinant CyaAs were not modified and these molecules displayed a hemolytic activity similar to that of wild type adenylate cyclase (17).

Immunization with HPV16-E7 Recombinant CyaAs Induces E7-Specific CTL Responses.

To test whether CyaA can induce CTL responses against HPV16-E7 epitopes, C57BL/6 mice were immunized once, intravenously with 50 µg of the different HPV16-E7 recombinant CyaAs. Splenocytes were harvested and stimulated in vitro with 1 μg/ml of the E7$_{43-77}$ peptide. Their ability to lyse TC-1 cells was determined 5 days later using a $^{51}$Cr release assay. As shown in FIG. 2A, a single i.v. immunization of C57BL/6 mice with HPV16-E7 recombinant CyaAs induced strong and specific CTL responses to TC-1 cells. Immunization with CyaA containing the full HPV16-E7 protein (FIG. 2A, b) or its deleted form, CyaA-E7$_{Δ30-42}$ (FIG. 2A, c), resulted in higher maximal CTL activities as compared to that induced by CyaA-E7$_{49-57}$ that contains only the minimal H-2D$^b$ restricted epitope (FIG. 2A, a), although we could not demonstrate statistical significance from our data. Similar results were obtained when peptide E749-57 was used for in vitro restimulation (data not shown). Splenocytes from mice vaccinated with a recombinant CyaA carrying a non relevant epitope(OVA$_{257-264}$) and restimulated in vitro with 1 μg/ml E7$_{43-77}$ peptide yielded only a weak non specific TC-1 cell lysis (FIG. 2A, a). It has been previously shown that the delivery of the OVACD8$^+$ cell epitope (SIINFEKL; SEQ ID NO: 15) to the MHC class I molecule by CyaA in vivo was dependent on TAP1 function (15). We tested whether this is also the case using CyaA-E7$_{Δ30-42}$. As shown in FIG. 2A, d, in vitro stimulated splenocytes from i.v. vaccinated TAP1$^{-/-}$ mice, were unable to lyse TC-1 cells. We also tested the requirement of CD4$^+$ T cell help in the in vivo priming of CTL response by HPV16E7-containing recombinant CyaA. In agreement with earlier observations (15), we observed that i.v. vaccination of MHC Class 11$^{-/-}$ mice using CyaA-E7$_{Δ30-42}$, resulted in the induction of high level of specific CTL responses to TC-1 cells (FIG. 2A, e). In contrast, we observed in this model some dependence towards CD40 signaling, as we observed a low level of CTL response to TC-1 cells in CD40$^{-/-}$ mice (FIG. 2A,f).

To estimate ex vivo the frequencies of HPV16-E7-specific splenocytes in mice immunized with recombinant CyaAs, the number of cells producing IFN-γ in response to in vitro stimulation with HPV16-E7$_{49-57}$ peptide was quantified by enzyme-linked immunospots (ELISPOT). FIG. 2B shows that there was only a slight difference in the number of IFN-γ-producing splenocytes specifically producing IFN-γ obtained from mice immunized with CyaE5-CysOVA as compared to those immunized with CyaA-E7$_{49-57}$. In contrast, the number of IFN-γ-producing splenocytes obtained was much more higher (p<0.05) in mice vaccinated with HPV16-E7 recombinant CyaAs containing either the full HPV16-E7 protein or its deleted form. The observed responses were epitope specific as very few spleen cells from these mice produced IFN-γ in the absence of stimulation by the HPV16-E7$_{49-57}$ peptide (FIG. 2B). These results show that CyaA is able to deliver in vivo the immunodominant CD8$^+$ H-2D$^b$-restricted T-cell epitope of the HPV16-E7 protein into the cytosol of immunocompetent cells for processing and presentation into the MHC class I pathway, to elicit strong CTL responses. In accordance with previous observations (25, 31), we confirm that CyaA is tolerant to insertion of large polypeptidic fragments as CyaAs carrying the full HPV16-E7 protein or its deleted and inverted form, were also able to induce strong CTL responses. Our data also demonstrate that these latter molecules induced significantly higher frequencies of HPV16-E7$_{49-57}$-specific responses in mice.

Immunization with HPV16-E7 Recombinant CyaAs Induces HPV16-E7 Specific Th1 Responses.

Th1 responses play an important role in protection against intracellular pathogens and tumor development (32, 33). We therefore characterized the type of T-cell responses induced by HPV16-E7 recombinant CyaAs. C57BL/6 mice were immunized once i.v. with 50 μg of the three different HPV16-E7 recombinant CyaAs, and cytokine synthesis was determined after in vitro stimulation of spleen cells with 10 μg/ml of the purified His-Tag HPV16-E7 protein. As shown in FIG. 3, immunization with CyaAs carrying the full HPV16-E7 protein or its deleted form resulted in a Th1-like profile characterized by the production of high levels of IFN-γ and the lack of detectable levels of IL-5. This response was specific since IFN-γ levels obtained after immunization with CyaA-E7$_{Full}$ or CyaA-E7$_{Δ30-42}$ were significantly higher than those obtained in mice mock-immunized with CyaAE5-CysOVA (p<0.05). However, this was not the case with splenocytes from mice immunized with CyaA-E7$_{49-57}$. Similar results were achieved when the restimulation was carried out with 1 μg/ml of E7$_{43-77}$ peptide (FIG. 3A, inset).

Taken together, these results indicate that, in our conditions, CD4$^+$ T cells play an important role in the secretion of IFN-γ as levels obtained with CyaAs carrying the full HPV16-E7 protein which contains class II H-2$^b$ restricted T cell epitopes, are much higher than those obtained with CyaA-E7$_{49-57}$ which contains only the class I H-2D$^b$ restricted epitope.

Immunization with HPV16-E7 Recombinant CyaAs Induces Regression of Established HPV16-Expressing Tumors.

Considering the robust immunological responses obtained, we then evaluated in vivo the therapeutic activity of HPV16-E7 CyaAs in a pre-clinical model consisting of a H-2$^b$ tumorigenic cell line expressing HPV16-E6 and E7 proteins (TC-1 cells) which is injected subcutaneously to C57BL/6 mice. In this model, it has been previously shown that tumor rejection is exclusively mediated by E7$_{49-57}$-specific CD8$^+$ T-cells (21, 22, 34, 35). Thus, 5×10$^4$ TC-1 cells were injected s.c. in the right flank of C57BL/6 mice and 50 μg of CyaAE5-HPV16-E7$_{49-57}$, -E7$_{full}$ or -E7$_{Δ30-42}$ were injected intravenously to mice 1, 5 or 10 days later. FIG. 4 represents the tumor growth in mice treated therapeutically 10 days after tumor grafting. Of note, in these conditions 100% of the animals developed palpable tumors by the time vaccination was given. To avoid unnecessary suffering, animals were sacrificed when tumor sizes reached 1000 mm$^3$. All untreated animals, as well as mice who were treated with a mock CyaAE5-cysOVA developed tumors of that size (>1000 mm$^3$) within a maximum of 49 days. In sharp contrast, the majority of animals treated with HPV16-E7 recombinant CyaAs remained tumor free throughout the duration of the experiment (FIG. 4, C, D, E. FIG. 5 shows the plot of the survival of the animals grafted with TC-1 cells and submitted to three different therapeutic protocols in which the recombinant CyaAs were injected at either day 1, day 5 or day 10 after the TC-1 graft. The medians survival times of untreated or mock-treated animals were comprised between 31 to 40 days. In contrast, the survival of mice vaccinated with CyaAs carrying HPV16-E7 antigens was significantly superior to that of control animals (p<0.05). Differences in the protective activities of the various constructs could be established although the statistical significance could not, because of the small size of the different samples. If the rate of tumor regression conferred by CyaA-E7$_{49-57}$ and -E7$_{Full}$ could not be noticeably differentiated, CyaA-E7$_{Δ30-42}$ was clearly superior in terms of tumor regression and growth inhibition, since in all the three therapeutic schemes, the protection rate was always higher than 90%.

Some animals vaccinated with CyaA-E7$_{49-57}$ and CyaA-E7$_{Full}$ appeared to grow tumors lately in the time course of the experiment (FIG. 4 (*) and data not shown). Bearing in mind that this phenomenon could reflect tumor escape mechanisms, we explanted the growing tumors from these animals and analyzed these cell lines named TC-1 A1 and TC-1 A2 by FACS analysis for H-2D$^b$ expression. As shown in FIG. 6, as compared to their native counterpart, TC-1 A1 and A2 cells explanted from late growing tumors had lost the expression of H-2D$^b$, thus most probably rendering them undetectable to E7$_{49-57}$-specific CD8$^+$ T-cells. Since TC-1 cells grew in vivo in an environment without antibiotic pressure for selection, we also checked by western blot for the expression of HPV16-E7 in TC-1 A1 and A2 cells. We could not find any difference in expression of this protein between TC-1 and TC-1 A1 and A2 cells (data not shown).

Taken together, these results demonstrate the efficiency of the adenylate cyclase vector as a suitable therapeutic vaccine for inducing the regression of HPV16-expressing tumors in a pre-clinical model.

We tested another injection route of clinical interest. Hence, 10 μg of CyaA-E7$_{\Delta 30-42}$ were injected i.d. twice at a 7-days interval starting 10 days after TC-1 graft. Interestingly, as all untreated and mock-treated animals developed tumors, we observed tumor regression in all of the animals treated with CyaA-E7$_{\Delta 30-42}$ (FIG. 4B, a, b). This therapeutic immunization resulted in a 100% survival at 90 days of the CyaA-E7$_{\Delta 30-42}$-treated mice whereas the survival medians of untreated and mock-treated animals were 30 and 32 days, respectively (FIG. 4, c).

Long Term Persistence of HPV16-E7$_{49-57}$ Specific CD8$^+$ T-Cells Induced by CyaA Immunization.

To assess the persistence of immune response induced by HPV16-E7 recombinant CyaAs, mice surviving from therapeutic experiments after 3 months were sacrificed and their splenocytes subjected to in vitro stimulation for five days with 1 μg/ml E7$_{43-77}$ peptide. Their ability to lyse TC-1 cells was then determined by a $^{51}$Cr release assay. As shown in FIG. 7, specific CTL responses to HPV16-E7$_{43-77}$ peptide were still demonstrated from splenocytes of animals immunized three months ago. Based on the maximum percentage of specific lysis at 30:1 ratio effector:target, the immunological response appeared to be more robust in animals treated with CyaA-E7$_{30-42}$, although no statistical significance could be demonstrated from these data. To assess the physiological relevance of such a long lasting immunogenicity, remaining animals were re-challenged s.c. with 5×10$^4$ TC-1 cells at day 100. Under such conditions, all naive age-matched control animals developed tumors and displayed a survival median time of 37.5 days (FIG. 8). In contrast, mice immunized three months ago with HPV16-E7 recombinant CyaAs were very significantly protected from tumor development. As observed above, animals vaccinated with CyaAE5-HPV16-E7$_{\Delta 30-42}$ displayed a high level of protection. However, at variance with results obtained in the first set of therapeutic experiments, there is now a striking difference of protection between animals treated with CyaA-E7$_{49-57}$ and those treated with CyaA-E7$_{Full}$ in favor of the latter, although the small size of the samples did not allow to unequivocally demonstrate a statistical significance. These observations suggest that in this model, T-cell help provided by CyaA carrying the full HPV16-E7 protein is of importance for efficient long lasting responses against TC-1 cells.

Taken together, our results demonstrate that one i.v. injection of 50 μg of recombinant CyaAs bearing the helper epitope of the HPV16-E7 protein (DRAHYNIVTF; SEQ ID NO: 16) is sufficient to induce long lasting E7$_{49}$-57 specific CD8$^+$ T cells that are capable of conferring protection against two TC-1 tumor cells challenges over a period of time of at least 6 months.

Therapeutic Efficacy of CyaA-E7$_{\Delta 30-42}$ Compares Favorably to that of Peptide Administered with CpG-ODN 1826.

To better evaluate the potency of CyaA as an antigen delivery system, we compared the therapeutic efficacy of CyaA-E7$_{\Delta 30-42}$ to that of HPV16-E7$_{43-77}$ peptide supplemented with CpG-ODN 1826 (37). Mice were therefore injected s.c. with 5×10$^4$ TC-1 cells and treated therapeutically 10 and 17 days later via the intra-dermal route with 10 μg of CyaA-E7$_{\Delta 30-42}$ or 10 μg of HPV16-E7$_{43-77}$ peptide administered with 1 μg of CpG-ODN 1826. The survival rates were similar in these two groups (FIG. 9), although results obtained with CyaA-E7$_{\Delta 30-42}$ were slightly better but not statistically different from those obtained with HPV16-E7$_{43-77}$ peptide mixed with CpG-ODN 1826. Of note, this result was obtained using 50 times more HPV16-E7$_{43-77}$ peptide than CyaA-E7$_{\Delta 30-42}$ on a molar basis. When used alone, the peptide HPV16-E7$_{43-77}$ had no effect on TC-1 tumor growth.

Prior Immunity to CyaA Vector Marginally Affects the Therapeutic Efficacy of CyaA-E7$_{\Delta 30-42}$.

In a clinical setting, multiple boosts will probably have to be given to patients with lesions in order to obtain efficient cellular immune responses. It is therefore essential to demonstrate that pre-immunity to the CyaA vector does not impair its ability to trigger tumor rejection. To do so, we immunized mice i.d. twice at a 7-days interval with 10 μg of empty vector CyaAE5, 90 or 30 days prior to s.c. injection with 5×10$^4$ TC-1 cells. Therapeutic treatment with two i.d. injections at a 7-days interval of 10 μg CyaA-E7$_{\Delta 30-42}$ was set on day 10. Analysis of antibody responses showed that empty vector immunized-mice were immune to CyaA at the time of TC-1 injection (FIG. 10A). We then compared the ability of CyaA-E7$_{\Delta 30-42}$ treatment to induce tumor rejection in age-matched naive animals and in CyaA immune animals. Whatever their immune status towards CyaA, the majority of mice treated with CyaA-E7$_{\Delta 30-42}$ remained tumor free throughout the experiment (FIG. 10B). Only 1 animal in the day-30 immune mice group and 2 in the day-90 immune mice group developed tumors (FIG. 10B b, d, f). In contrast, 100% of mock-treated animals developed tumors and were sacrificed (FIG. 10B, a, c, e). We did not observe any correlation between the level of anti-CyaA antibodies titers and the development of TC-1 tumors (data not shown). Furthermore, survival curves of the CyaA-E7$_{\Delta 30-42}$-treated mice (FIG. 10B, b, d, f) were not statistically different (p=0.324).

These data therefore indicate that the effect of pre-existing immunity towards CyaA has only very limited effect on the ability of this vector to subsequently induce efficient responses against a foreign given antigen.

DISCUSSION

Previous studies have demonstrated that the adenylate cyclase from *Bordetella pertussis* is a powerful tool to deliver in vivo, CD4$^+$ and CD8$^+$ T cell epitopes to the MHC-class II and I presentation pathways of dendritic cells. In experimental murine models, this system has been used to trigger efficient Th1 and CTL responses providing anti-viral and anti-tumoral protection (36). As an evaluation of the potential application of CyaA in humans for the treatment of HPV16-associated cervical malignancies, we went on to demonstrate that this vector efficiently delivers in vivo epitopes from the E7 protein from HPV16.

We constructed various HPV16 recombinant CyaAs containing the full E7 protein from HPV16 or sub-fragments of this polypeptide, including in particular the H-2D$^b$-restricted minimal CTL epitope corresponding to residues 49-57. We showed that these different recombinant proteins were able to prime specific and strong CTL responses when injected to C57BL/6 mice. Our data confirmed that the delivery of CTL epitopes by CyaA requires a fully functional Class I presentation pathway as we could not prime CTL upon injection of CyaA-E7$_{\Delta 30\text{-}42}$ in TAP1$^{-/-}$ mice (15). The CTL priming mediated by CyaA was independent of the presence of CD4$^+$ T cells as indicated by the efficient CTL responses obtained in MHC Class II$^{-/-}$ mice in agreement with previous results (15). This characteristic of CyaA as a vaccinal vector is of great importance when considering the vaccination of immunosuppressed or immunodeficient patients presenting an altered number of CD4$^+$ T cells. However, low CTL responses were obtained in CD40$^{-/-}$ mice indicating that CTL priming was partially dependent upon CD40 signaling. These observations suggest that HPV16-E7 recombinant CyaAs elicit MHC class I-restricted CTL directly by direct stimulation of professional APC. CD40-CD40L interaction is nonetheless required to obtain optimal priming of CTL responses.

We compared the immunogenicity of the minimal H-2D$^b$-restricted CTL epitope of HPV16-E7 to that of the full or the Δ30-42 E7 protein which contain among probably others, the described helper epitope DRAHYNIVTF (SEQ ID NO: 16) (37). The CTL priming as well as the frequencies of HPV16-E7-specific splenocytes induced by CyaA-E7$_{Full}$ and CyaAE-E7$_{\Delta 30\text{-}42}$ were superior to those induced by CyaA-E7$_{49\text{-}57}$ carrying only the CTL epitopes E$_{49\text{-}57}$. These observations indicate that simultaneous delivery of CTL and Th epitopes by CyaA results in more robust CTL response. This is in agreement with previously published data in other models at the pre-clinical (37) and clinical level (38). The delivery of HPV16-E7 Th epitopes by recombinant CyaAs was further evidenced by the analysis of the cytokine produced by HPV16-E7-specific splenocytes restimulated in vitro with recombinant HisTag-HPV16-E7 protein or E7$_{43\text{-}77}$ peptide. Indeed, we observed specific synthesis of IFN-γ only in mice vaccinated with recombinant HPV16-E7 CyaAs containing the Th epitope. The typical Th1 profile characterized by a high level of IFN-γ and no secretion of IL-5, that we observed after one i.v. immunization with CyaA-E7$_{Full}$ and CyaA-E7$_{\Delta 30\text{-}42}$ highlights the potential interest of this vector for tumor immunotherapy.

This was tested in a tumor rejection model based on s.c.-established tumorigenic TC-1 cells (21). In accordance with our data demonstrating the immunogenicity of HPV16-E7 recombinant CyaAs, we observed that these recombinant proteins were able to induce the regression of established TC-1 tumors. CyaA-E7$_{30\text{-}42}$ was superior to CyaA-E7$_{49\text{-}57}$ and CyaAE5-HPV16-E7$_{Full}$ in terms of survival over a period of 90 days. As CyaAs carrying the full and the Δ30-42 E7 protein yielded comparable results in terms of CTL priming capacity, frequencies of HPV16-E7$_{49\text{-}57}$ specific splenocytes and production of IFN-γ, we expected CyaA-E7$_{Full}$ to be superior to CyaA-E7$_{49}$-57 in terms of survival. A higher number of tested animals would have, most probably, help to rule out this apparent discrepancy. Yet, two aspects regarding the biochemistry of CyaA should be discussed here. First, the presence of negatively charged amino acid in the region 224-235 of CyaA was shown to inhibit the translocation of the catalytic domain of CyaA in the cytosol of eukaryotic cells (39). In this respect, the acidic E7 protein (pKi=4.17) might have precluded an efficient translocation of the N-terminal domain of CyaA into the cytosol of DC. CyaA-E7$_{\Delta 30\text{-}42}$ has been specifically designed to remove a stretch of negatively charged amino acids located between residues 30 to 42 (DSSEEEDEIDGPA; SEQ ID NO: 17) in order to favor its delivery into DC (and furthermore two positively charged amino acids (KR) were introduced at each side of the inserted N-terminal domain of HPV16-E7. Second, Gmira et al. (25) have demonstrated that unfolding of the heterologous protein inserted within CyaA is mandatory to allow internalization of the recombinant protein into the target cells. The insertion of two different fragments of the E7 polypeptide into two different permissive sites in CyaA-E7$_{\Delta 30\text{-}42}$ may prevent E7 folding and thus should facilitate its translocation into target cells.

In the time course of tumor rejection experiments, some mice started lately to grow HPV16 positive tumors after having previously rejected established TC-1 tumors. FACS® analysis revealed that cells from these tumors did not express H-2D$^b$ molecules. This observation leads to consider the possibility of a homologous boosting of recombinant CyaA vaccination so as to eradicate more strikingly tumor cells and to prevent tumor relapse via escape mechanisms. Bearing in mind data from other teams in the field (37, 40, 41), it would be relevant to boost CyaA vaccination in mice rising the total amount of injected recombinant HPV16-E7 CyaA to 100 µg, i.e. 0.56 nmoles. Experiments intended to test this latter observation, as well as others to test different ways of CyaAs administration are being conducted.

Upon re-challenge with TC-1 cells, surviving mice immunized with HPV16-E7 recombinant CyaAs were selectively protected. This was correlated with the presence of HPV16-E7$_{49\text{-}57}$ CD8$^+$ T-cells among the splenocytes of these animals. This observation strengthened the fact that late relapses observed in FIG. 4, were due to tumor escape mechanisms and not to waning immunity towards the E7 protein. The better survival rate of mice immunized with recombinant CyaAs containing Th epitopes indicated that providing T-cell help against the same antigen also results in an efficient recall of HPV16-E7$_{49\text{-}57}$ CD8$^+$ T-cells. In this respect, it has been proposed that CD4$^+$ T cells, through CD40L may imprint a unique molecular signature on effector CD8$^+$ T cells, endowing them with their capacity for improved cell function (42).

In a validated model for the testing of novel immunotherapeutics for the treatment of HPV-associated neoplasia (21), we have demonstrated that CyaA is an efficient vector to induce the regression of established tumors as well as to provide protection against tumorigenic challenge for over a long period of time. Unlike other approaches that are currently developed (11), CyaA-based immunotherapy precludes the need to select HLA restricted epitopes as full proteins can be inserted, and avoids the use of viral vectors and/or potentially oncogenic HPV DNA sequences. Furthermore, we obtained best results with a CyaA that contains two sub-fragments of HPV-E7 inserted into two different permissive sites of CyaA.

The fact that this latter construction includes all the HPV16-E7 HLA class I and class II epitopes described in the literature (8, 46) strengthens the selection of CyaA-E7$_{\Delta 30\text{-}42}$ in vaccine applications.

Based on the data presented here, we plan to test the efficacy of CyaA containing HPV16-E7 in clinical trials targeting cervical and anal dysplasias associated with HPV infection.

Example 2

The objective was to make a bivalent therapeutic vaccine that target both HPV16 and HPV18 E7 proteins to treat HPV16 and HPV18-associated malignancies in humans. Vaccine candidates termed CyaAE5-HPV16E7$_{\Delta 30\text{-}42}$ and CyaAE5-HPV18E7$_{\Delta 32\text{-}42}$ have therefore been designed, constructed, produced and purified. HHD mice are H-2D$^{-/-}$, β2m$^{-/-}$ double-knockout mice expressing the HHD transgene comprising the α1 (H) and α2 (H) domains of HLA*0201 linked to the α3 transmembrane and cytoplasmic domains of H-2D$^b$ (D), with the α1 domain linked to human β2-microglobulin. Thus, the only MHC class I molecule expressed by the HHD mice is the modified HLA*0201 molecule (Pascolo et Lemonnier).

The goal of this experiment was to demonstrate:
1—that recombinant CyaA is able to deliver HLA-A2 restricted epitopes of HPV16 and HPV18 E7 proteins.
2—There is no phenomenon of immuno-dominance of one HPV recombinant cyaA over the other.

To do so, HHD mice were vaccinated i.v. with 50 μg of CyaAE5-HPV16E7$_{\Delta 30\text{-}42}$ (3 mice), CyaAE5-HPV18E7$_{\Delta 32\text{-}42}$ (3 mice) or with CyaAE5-HPV16E7$_{\Delta 30\text{-}42}$+CyaAE5-HPV18E7$_{\Delta 32\text{-}42}$ in the same (retro-orbital) injection (50 μg in 200 μl) (5 mice). Seven days later, pooled splenocytes were restimulated in vitro with HLA-A2 peptides from HPV16E7 or HPV18E7 either described in the literature or estimated from the SYFPEITHI software.

CTL activity was assayed 5 days later using $^{51}$Cr release. Targets cells were HHD-EL4 cells, loaded or not with the different relevant peptides.

Results show that, vaccination with CyaAE5-HPV16E7$_{\Delta 30\text{-}42}$ or CyaAE5-HPV18E7$_{\Delta 32\text{-}42}$, induced the specific lysis of EL4-HHD cells loaded with HPV16E7 or HPV18E7 peptide following autologous peptidic in vitro restimulation.

This result also demonstrates that co-injection of CyaAE5-HPV16E7$_{\Delta 30\text{-}42}$ together with CyaAE5-HPV18E7$_{\Delta 32\text{-}42}$ does not impair the immunogenicity of any of the HPV recombinant CyaA as similar responses to relevant peptides were observed.

This result demonstrates that CyaAE5-HPV16E7$_{\Delta 30\text{-}42}$ and CyaAE5-HPV18E7$_{\Delta 32\text{-}42}$ are able to induce in vivo a cytotoxic response to human HLA-A2 restricted epitopes of respective E7 protein.

Mice

Specific pathogen free HHD mice were bred at the Pasteur Institute. Eleven 6-10-week old males were used for this experiment.

Reagents and Biological Material
Reagents and Buffers
RPMI 1640 medium-glutamax (invitrogen GIBCO, ref: 6187010)
Ethanol 70° (Prolabo, ref: MC311631)
Penicillin-streptomycin (invitrogen GIBCO, ref: 15140122)
Foetal Bovine Serum (FBS) (PERBIO, ref: CH30160.03)
β mercapto-ethanol (BIO-RAD, ref: 161-0710)
Pyrolyzed water
Blue trypan (SIGMA, T-8154)
51Cr
Trilux Scintillant (Wallac)
Peptides Five synthetic peptides (Neosystem, Strasbourg, France) were used in for in vitro stimulation of splenocytes prior to the $^{51}$Cr release assay:

E7$_{11\text{-}20}$(YMLDLQPETT (SEQ ID NO: 18), one-letter code for amino acid, #253) corresponding to a HPV16-E7 HLA-A2-restricted epitope (1), E7$_{82\text{-}90}$ (LLMGTLGIV (SEQ ID NO: 19), #258) corresponding to aHPV16-E7 HLA-A2-restricted epitope (1), E7$_{86\text{-}93}$ (TLGIVCPI (SEQ ID NO: 20), #255) corresponding to a HPV16-E7 HLA-A2-restricted epitope (1), E7$_{7\text{-}15}$ (TLQDIVLHL (SEQ ID NO: 21), #251) corresponding to a HPV18-E7 HLA-A2-restricted epitope predicted by SYFPEITHI software, E7$_{86\text{-}94}$ (FQQLFLNTL (SEQ ID NO: 22), #257) corresponding to a HPV18-E7 HLA-A2-restricted epitope (2).

Peptides have been diluted at 1 mg/ml in sterile, apyrogenic water (#253, 255, 251) or apyrogenic water, 0.1 M NaHCO$_3$; acetonitrile (50/50) (#257 and 258).

Recombinant Adenyl Cyclases (CyaA)
Two CyaA have been tested in this experiment:
CyaA-HPV16E7$_{\Delta 30\text{-}42}$
CyaA-HPV18E7$_{\Delta 32\text{-}42}$ These CyaA were expressed in E. coli strain BLR by using derivatives of plasmid pTRACE5 coding for an enzymatically inactive CyaA (CyaAE5). Construction of plasmids, production and purification of all recombinant proteins are made as described above in Example 1 relating to construction and purification of recombinant B. pertussis adenylate cyclase carrying HPV16-E7 epitopes, however with the epitopes used for the present experiment.

Stock solutions (stored at −20° C.) containing respectively 1.22 mg/ml and 1.33 mg/ml of CyaA in 8 M urea, were thawed and diluted at 250 μg/ml with PBS (Gibco BRL) before i.v. administration to mice. The final concentration of urea was thus between 1.6 and 1.5 M, respectively.

Cell Lines

EL4-HHD cells were used as targets in $^{51}$Cr CTL assay.

These cells were maintained in complete medium RPMI 1640 with Glutamax supplemented with 10% heat-inactivated FCS, 100 U/ml penicillin, 100 μg/ml streptomycin, and $5.10^{-5}$ M β2-mercaptoethanol (Gibco BRL, Cergy-Pontoise, France).

Methods
Mouse Immunization

Vigil animals were immunized with one intravenous (retro-orbital) injection (50 μg in 200 μl) of CyaAE5-HPV16E7$_{\Delta 30\text{-}42}$ and/or CyaAE5-HPV18E7$_{\Delta 32\text{-}42}$ with 0.3 ml insulin Syringes (Terumo).

Experimental Plans

The table 1 describes vaccine candidates and treatments administered to each group of mice.

TABLE 1

| Experimental group definition: CTL induction Induction of CTL (CTL Assay) | | |
|---|---|---|
| Number of mice | CyaAE5 | Immunization dose/Volume/Urea concentration |
| 3 | CyaA-HPV16E7$_{\Delta 30\text{-}42}$ | 50 μg/200 μl/1.6 M |
| 3 | CyaA-HPV18E7$_{\Delta 32\text{-}42}$ | 50 μg/200 μl/1.5 M |
| 5 | CyaA-HPV16E7$_{\Delta 30\text{-}42}$ and CyaA-HPV18E7$_{\Delta 32\text{-}42}$ | 50 μg of each/200 μl/3.1 M |

CTL Assay

For in vitro evaluation of the cellular immune response induced by immunization, euthanized animals (CO$_2$) were splenectomized 7 days after immunization. Splenocytes from each group were pooled before CTL assay.

Stimulation of CTLs (Prepare 2 Flasks T25 per Spleen)
Sample spleens and crush them in RPMI 1640-Glutamax 1% Ab.

Decant

Centrifuge at 1200 rpm for 10 minutes.

Resuspend cells in 2 ml RMPI 1640-Glutamax 1% Ab-10% FCS-5.10-5M (β mercapto-ethanol (complete medium: CM)

In each T25 Flask, put:
10 ml of CM
$5.10^7$ effector cells
Relevant peptide at 10 µg/ml final concentration
Incubate for 5 days without moving the flasks
Cytotoxicity Assay
1/Target Cells:
The day before, dilute target cells 1/3 or 1/2 so as to harvest them in exponential growth
Transfer to 15 ml tubes.
Centrifuge at 1200 rpm for 10 minutes
Resuspend in 1 ml of RPMI 1640-1% Ab
Numerate.
Prepare 2 tubes: one with peptide, one without peptide.
Resuspend in 150 µl:
  peptide (50 µmolar) in one of the two tubes.
  100 µCi of $^{51}$Cr (50 µl) for $3\,10^6$ cells.
  Medium up to 150 µl.
Incubate for 1 hour in waterbath at 37° C., gently shake every 15 minutes.
2/Effector Cells
Discard about 5 ml of supernatant with pasteur pipette.
Resuspend thoroughly cells by pipetting.
Centrifuge at 1200 rprm for 10 minutes
Resuspend in 1 ml of CM. Numerate.
Adjust to $10^7$ cells/ml.
Dilute so as to obtain following effector/target ratios: 200/1, 100/1, 50/1, 25/1, 12/1, 6/1
Distribute 100 µl/well in U-bottom microtiter plate.
Incubate at 37° C. 7.5% $CO_2$ while finishing the preparation of target cells
3/Assay:
Wash target cells with 10 ml of RPMI 1640-1% Ab
Wash again with 10 ml of CM.
Resuspend in 2 ml of CM
Numerate
Adjust to $10^5$ cells/ml
Distribute 100 µl/well.
Prepare 6 wells for spontaneous release (Adjust to 100 µl in CM)
Prepare 6 wells for maximum release (Add 100 µl of 20% Triton X-405)
Incubate at 37° C. 7.5% $CO_2$ for 4 to 5 hours.
4/Counting:
Centrifuge 5 to 10 minutes at 2000 rpm.
Put 100 µl of Trilux scintillant in a floppy P96 microtiter plate
Sample 50 µl of supernatant and transfer it to the floppy plate.
Seal the plate with plastic film tape.
Count the following day in a wallac counter.
HPV16E7 CTL Specific Responses
CTL responses induced by CyaA-HPV16E7$_{\Delta 30-42}$ is shown in FIG. 11.
HPV18E7 CTL Specific Responses
CTL responses induced by CyaA-HPV18E7$_{\Delta 32-42}$ is shown in FIG. 12.

Conclusion

Both CyaA-HPV16E7$_{\Delta 30-42}$ and CyaA-HPV18E7$_{\Delta 32-42}$ are able to induce specific CTLs towards respective HLA-A2 restricted peptides in this chimeric HHD model.
Co-injection of CyaA-HPV16E7$_{\Delta 30-42}$ and CyaA-HPV18E7$_{\Delta 32-42}$ did not interfere with each individual CyaA's ability to induce CTLs against respective specific HLA-A2 restricted peptides. This indicates that there is no phenomenon of immunodominance of one construction towards the other. This constitutes a crucial observation in regards to the strategy to make-up a bivalent vaccine.

Example 3

Construction and Immunological Evaluation of Recombinant Adenylate Cyclases Containing the E7 Protein from HPV18 and the E7 Proteins from HPV16 and HPV18

Carcinomas of the anogenital tract account for nearly 12% of all cancers in women, making cervical carcinoma (CxCa) the second most frequent gynecological cancer in the world. The critical observation that infection with human papillomavirus (HPV) might be the causative agent for CxCa was subsequently confirmed by epidemiological studies. The most prevalent HPV types associated with CxCa are HPV16 and HPV18 (55% and 12% prevalence, respectively) {Clifford, 2003}. In order to cover a larger population, it was decided to construct a bivalent therapeutic vaccine carrying E7 from HPV16 and HPV18. Two possible strategies have been tested; (i) the first one to mix equimolar quantities of two recombinant CyaAs carrying E7 from HPV16 on one hand and E7 from HPV18 on the other; (ii) the second one is to construct a recombinant CyaA carrying both E7 proteins from HPV16 and HPV18. The present report describes the construction of recombinant CyaAs carrying E7 from HPV18 or E7 from both viruses. The immunogenicity of the constructions were tested in a CTL assay.

Epitope Identification

The amino-acid sequence of HPV18E7 was submitted to SYFPEITHI while searching for H-$2^b$ epitopes. This software uses an algorithm to predict epitopes that may bind to a defined MHC molecule. The software returned a putative epitope restricted by the H-2D$^b$ molecule with a score of 25. Usually we consider epitopes when their score is above 22. The putative peptide IDGVNHQHL (SEQ ID NO: 3) was therefore synthesized by Neosystem.

Constructions of Recombinant CyaAs

The scheme representing the strategy use to construct the plasmids to produce CyaA-HPV18E7, CyaA-HPV18E7$_{\Delta 32-42}$, CyaA-HPV16+18E7, CyaA-HPV16+18ΔE7, are shown in FIGS. 13 and 14.

CTL Assay

The goal of this experiment was to demonstrate the in vivo induction of CTL by recombinant CyaA carrying the either fragments or the entire HPV18E7 protein as well as both HPV16 and HPV18 E7 proteins. The H-2D$^b$ epitope targeted are HPV18E7$_{41-49}$ (IDGVNHQHL; SEQ ID NO: 3) obtained from computer predictive software and HPV16E7$_{49-57}$. C57BL/6 mice were vaccinated i.v. with 50 µg of CyaA-CysOVA, CyaA-HPV18E7, CyaA-HPV18E7$_{\Delta 32-42}$, CyaA-HPV16+18E7 or CyaA-HPV16+18ΔE7 (2 in each group). 7 days later, pooled splenocytes were restimulated in vitro with peptides HPV18E7$_{41-49}$ (10 g/ml), OVA257-264 (1 g/ml) or HPV16E7$_{43-77}$ (1 µg/ml). CTL activity was assayed 5 days later using 51 Cr release. Targets cells were EL4 cells loaded or not with HPV18E7$_{41}$-49 peptide (8-nmol) or TC-1 cells. The legend in the figures indicate: vaccination/restimulation. Example: OVA/OVA refers to mice vaccinated with CyaAE5-CysOVA and restimulated with the OVA peptide.

These results (FIG. 16) show that, in contrast to CyaA-HPV18E7$_{Full}$, CyaA-HPV18E7$\Delta_{32-42}$ is able to deliver in vivo a computer predicted CD8+H-2D$^b$-restricted T-cell epitope of the HPV18-E7 protein into the cytosol of immunocompetent cells for processing and presentation into the MHC class I pathway, to elicit strong CTL responses. It is odd that CyaA-HPV18E7$\Delta_{32\text{-}42}$ is able to prime CTL response against HPV18E7$_{41\text{-}49}$ because this recombinant CyaA lacks the first two amino acids of the peptide HPV18E7$_{41\text{-}49}$. However at the insertion site of HPV18E7 fragment 43 to 105, there are one alanine and one serine so that the putative peptide is now ASGVNHQHL (SEQ ID NO: 4) instead of IDGVNHQHL (SEQ ID NO: 3). When subjected to syfpeithi this peptide came out with a score of 29 (25 for the native one). It is therefore likely that by substituting the first to amino-acids of this peptide by our cloning we have rendered it from cryptic to immunogenic. This is the first time that an epitope for the HPV18E7 protein is described in the H-2D$^b$ context.

Despite a high level of non specific background, these results also show that, CyaA-HPV16+18E7$_{Full}$ and CyaA-HPV16+18E7$_\Delta$ are able to deliver in vivo the H-2D$^b$-restricted T-cell epitope of the HPV16-E7 protein into the cytosol of immunocompetent cells for processing and presentation into the MHC class I pathway to elicit strong CTL responses. CyaA-HPV16+18E7$_\Delta$ display a greater ability to do so as compared to that of CyaA-HPV16+18E7$_{Full}$. These data also show for the first time that CyaA carrying large polypeptidic fragments (up to 203 amino acids) is still immunogenic.

Figure 16:
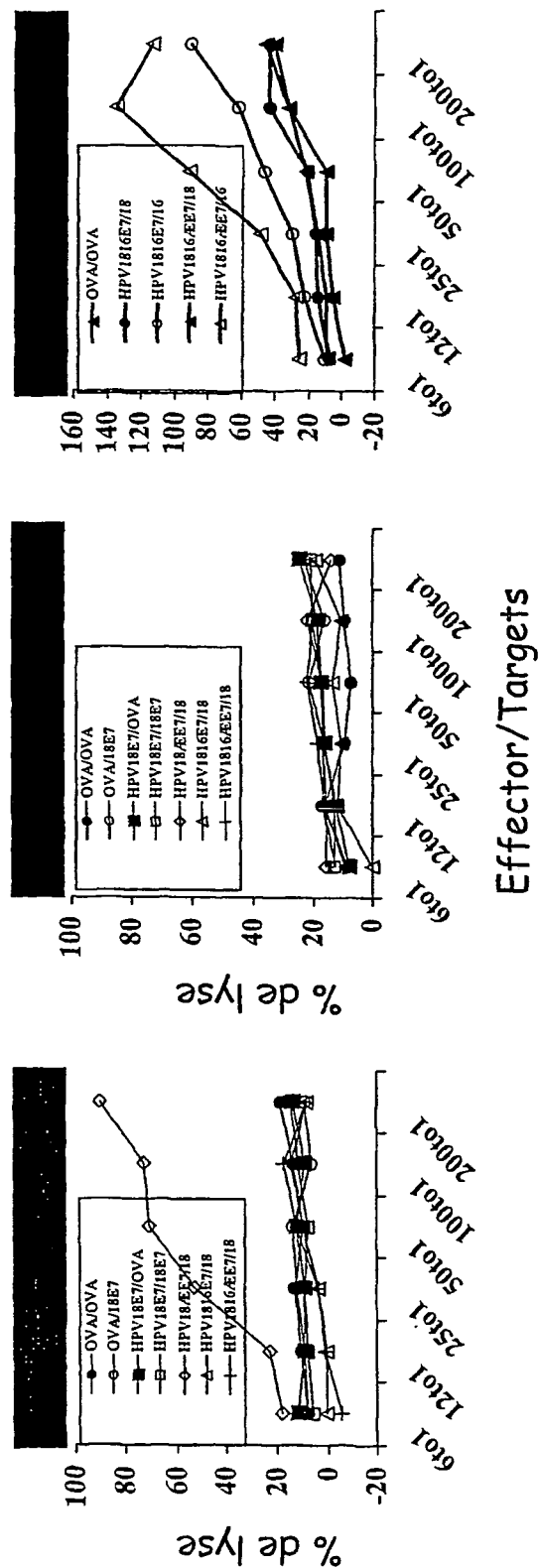

A further experiment was done in order to confirm that described in FIG. 16. The two remaining mice in each group were treated separately from the first ones. The experimental set-up is similar. The conclusions are identical to those in FIG. 16 except that the high level of non specific lysis of EL4 cells by CTLs from CyaAE5-HPV18E7$_{\Delta 32\text{-}42}$ vaccinated mice is likely to be due to an excess of HPV18E7$_{41\text{-}49}$ peptide remaining in the flasks.

There is also a lysis of TC-1 cells with splenocytes from mice vaccinated with CyaA-HPV16+18$\Delta$E7 but not with CyaA-HPV16+18E7 this time. In this experiment, the non-specific background peaks at 40%. Nevertheless the conclusions that can be drawn from FIG. 17 confirm those drawn from FIG. 16, that is:

CyaA-HPV18E7$_{\Delta 32\text{-}42}$ is able to deliver in vivo a computer predicted CD8$^+$ H-2D$^b$-restricted T-cell epitope of the HPV18-E7 protein into the cytosol of immunocompetent cells for processing and presentation into the MHC class I pathway, to elicit strong CTL responses. This is the first time that an epitope for the HPV18E7 protein is described in the H-2D$^b$ context.

Recombinant CyaA carrying large polypeptidic fragments (up to 203 amino acids) is still immunogenic.

Conclusion

It was decided to construct a bivalent therapeutic vaccine carrying E7 from HPV16 and HPV18. Two possible strategies have been considered; (i) the first one to mix equimolar quantities of two recombinant CyaAs carrying E7 from HPV16 on one hand and E7 from HPV18 on the other; (ii) the second one is to construct a recombinant CyaA carrying both E7 proteins from HPV16 and HPV18. The present results describe the construction of recombinant CyaAs carrying E7 from HPV18 or E7 from both viruses. The immunogenicity of the constructions were tested in a CTL assay.

The main conclusion from this study is that both considered strategies are feasible since, recombinant CyaA carrying HPV18E7 sub-fragments is functional as it revealed for the first time a cryptic H-2D$^b$-restricted epitope within the sequence of HPV18E7. Moreover recombinant CyaAs carrying E7 proteins (or sub-fragments) from both HPV16 and 18 viruses were still and most interestingly immunogenic as they were able to prime CTL response against H-2D$^b$-restricted HPV16E7 epitopes naturally presented by TC-1 cells.

REFERENCES 1. zur Hausen, H. Papillomaviruses and cancer: from basic studies to clinical application. Nat Rev Cancer, 2: 342-350, 2002.
2. Clifford, G. M., Smith, J. S., Plummer, M., Munoz, N., and Franceschi, S. Human papillomavirus types in invasive cervical cancer worldwide: a meta-analysis. Br J Cancer, 88: 63-73, 2003.
3. Frazer, I. H. Prevention of cervical cancer through papillomavirus vaccination. Nat Rev Immunol, 4: 46-55, 2004.
4. de Gruijl, T. D., Bontkes, H. J., Walboomers, J. M., Stukart, M. J., Doekhie, F. S., Remmink, A. J., Helmerhorst, T. J., Verheijen, R. H., Duggan-Keen, M. F., Stern, P. L., Meijer, C. J., and Scheper, R. J. Differential T helper cell responses to human papillomavirus type 16 E7 related to viral clearance or persistence in patients with cervical neoplasia: a longitudinal study. Cancer Res, 58: 1700-1706, 1998.
5. Evans, E. M., Man, S., Evans, A. S., and Borysiewicz, L. K. Infiltration of cervical cancer tissue with human papillomavirus-specific cytotoxic T-lymphocytes. Cancer Res, 57: 2943-2950, 1997.
6. Nimako, M., Fiander, A. N., Wilkinson, G. W., Borysiewicz, L. K., and Man, S. Human papillomavirus-specific cytotoxic T lymphocytes in patients with cervical intraepithelial neoplasia grade III. Cancer Res, 57: 4855-4861, 1997.
7. Ressing, M. E., van Driel, W. J., Celis, E., Sette, A., Brandt, M. P., Hartman, M., Anholts, J. D., Schreuder, G. M., ter Harmsel, W. B., Fleuren, G. J., Trimbos, B. J., Kast, W. M., and Melief, C. J. Occasional memory cytotoxic T-cell responses of patients with human papillomavirus type 16-positive cervical lesions against a human leukocyte antigen-A *0201-restricted E7-encoded epitope. Cancer Res, 56: 582-588, 1996.
8. van der Burg, S. H., Ressing, M. E., Kwappenberg, K. M., de Jong, A., Straathof, K., de Jong, J., Geluk, A., van Meijgaarden, K. E., Franken, K. L., Ottenhoff, T. H., Fleuren, G. J., Kenter, G., Melief, C. J., and Offringa, R. Natural T-helper immunity against human papillomavirus type 16 (HPV16) E7-derived peptide epitopes in patients with HPV16-positive cervical lesions: identification of 3 human leukocyte antigen class II-restricted epitopes. Int J Cancer, 91: 612-618, 2001.
9. Schreurs, M. W., Scholten, K. B., Kueter, E. W., Ruizendaal, J. J., Meijer, C. J., and Hooijberg, E. In vitro generation and life span extension of human papillomavirus type 16-specific, healthy donor-derived CTL clones. J Immunol, 171: 2912-2921, 2003.
10. Welters, M. J., de Jong, A., van den Eeden, S. J., van der Hulst, J. M., Kwappenberg, K. M., Hassane, S., Franken, K. L., Drijfhout, J. W., Fleuren, G. J., Kenter, G., Melief, C. J., Offringa, R., and van der Burg, S. H. Frequent display of human papillomavirus type 16 E6-specific memory T-Helper cells in the healthy population as witness of previous viral encounter. Cancer Res, 63: 636-641, 2003.
11. Roden, R. and Wu, T. C. Preventative and therapeutic vaccines for cervical cancer. Expert Rev Vaccines, 2: 495-516, 2003.
12. Ladant, D. and Ullmann, A. *Bordetella pertussis* adenylate cyclase: a toxin with multiple talents. Trends Microbiol, 7: 172-176, 1999.
13. Morón, G., Dadaglio, G., and Leclerc, C. New tools for antigen delivery to the MHC class I pathway. Trends in Immunology, 25: 92-97, 2004.
14. Guermonprez, P., Khelef, N., Blouin, E., Rieu, P., Ricciardi-Castagnoli, P., Guiso, N., Ladant, D., and Leclerc, C.

14. The adenylate cyclase toxin of *Bordetella pertussis* binds to target cells via the alpha(M)beta(2) integrin (CD11b/CD18). J Exp Med, 193: 1035-1044, 2001.
15. Guermonprez, P., Fayolle, C., Rojas, M. J., Rescigno, M., Ladant, D., and Leclerc, C. In vivo receptor-mediated delivery of a recombinant invasive bacterial toxoid to CD11c+CD8 alpha-CD11bhigh dendritic cells. Eur J Immunol, 32: 3071-3081, 2002.
16. Fayolle, C., Ladant, D., Karimova, G., Ullmann, A., and Leclerc, C. Therapy of murine tumors with recombinant *Bordetella pertussis* adenylate cyclase carrying a cytotoxic T cell epitope. J Immunol, 162: 4157-4162, 1999.
17. Fayolle, C., Osickova, A., Osicka, R., Henry, T., Rojas, M. J., Saron, M. F., Sebo, P., and Leclerc, C. Delivery of multiple epitopes by recombinant detoxified adenylate cyclase of *Bordetella pertussis* induces protective antiviral immunity. J Virol, 75: 7330-7338, 2001.
18. Van Kaer, L., Ashton-Rickardt, P. G., Ploegh, H. L., and Tonegawa, S. TAP1 mutant mice are deficient in antigen presentation, surface class I molecules, and CD4-8+ T cells. Cell, 71: 1205-1214, 1992.
19. Madsen, L., Labrecque, N., Engberg, J., Dierich, A., Svejgaard, A., Benoist, C., Mathis, D., and Fugger, L. Mice lacking all conventional MHC class II genes. Proc Natl Acad Sci USA, 96: 10338-10343, 1999.
20. Kawabe, T., Naka, T., Yoshida, K., Tanaka, T., Fujiwara, H., Suematsu, S., Yoshida, N., Kishimoto, T., and Kikutani, H. The immune responses in CD40-deficient mice: impaired immunoglobulin class switching and germinal center formation. Immunity, 1: 167-178, 1994.
21. Lin, K. Y., Guarnieri, F. G., Staveley-O'Carroll, K. F., Levitsky, H. I., August, J. T., Pardoll, D. M., and Wu, T. C. Treatment of established tumors with a novel vaccine that enhances major histocompatibility class II presentation of tumor antigen. Cancer Res, 56: 21-26, 1996.
22. Feltkamp, M. C., Smits, H. L., Vierboom, M. P., Minnaar, R. P., de Jongh, B. M., Drijfhout, J. W., ter Schegget, J., Melief, C. J., and Kast, W. M. Vaccination with cytotoxic T lymphocyte epitope-containing peptide protects against a tumor induced by human papillomavirus type 16-transformed cells. Eur J Immunol, 23: 2242-2249, 1993.
23. Tindle, R. W., Fernando, G. J., Sterling, J. C., and Frazer, I. H. A "public" T-helper epitope of the E7 transforming protein of human papillomavirus 16 provides cognate help for several E7 B-cell epitopes from cervical cancer-associated human papillomavirus genotypes. Proc Natl Acad Sci USA, 88: 5887-5891, 1991.
24. Dadaglio, G., Morel, S., Bauche, C., Moukrim, Z., Lemonnier, F. A., Van Den Eynde, B. J., Ladant, D., and Leclerc, C. Recombinant adenylate cyclase toxin of *Bordetella pertussis* induces cytotoxic T lymphocyte responses against HLA*0201-restricted melanoma epitopes. Int Immunol, 15: 1423-1430, 2003.
25. Gmira, S., Karimova, G., and Ladant, D. Characterization of recombinant *Bordetella pertussis* adenylate cyclase toxins carrying passenger proteins. Res Microbiol, 152: 889-900, 2001.
26. Guermonprez, P., Fayolle, C., Karimova, G., Ullmann, A., Leclerc, C., and Ladant, D. *Bordetella pertussis* adenylate cyclase toxin: a vehicle to deliver CD8-positive T-cell epitopes into antigen-presenting cells. Methods Enzymol, 326: 527-542, 2000.
27. Franken, K. L., Hiemstra, H. S., van Meijgaarden, K. E., Subronto, Y., den Hartigh, J., Ottenhoff, T. H., and Drijfhout, J. W. Purification of his-tagged proteins by immobilized chelate affinity chromatography: the benefits from the use of organic solvent. Protein Expr Purif, 18: 95-99, 2000.
28. Dadaglio, G., Moukrim, Z., Lo-Man, R., Sheshko, V., Sebo, P., and Leclerc, C. Induction of a polarized Th1 response by insertion of multiple copies of a viral T-cell epitope into adenylate cyclase of *Bordetella pertussis*. Infect Immun, 68: 3867-3872, 2000.
29. Michallet, M. C., Preville, X., Flacher, M., Fournel, S., Genestier, L., and Revillard, J. P. Functional antibodies to leukocyte adhesion molecules in antithymocyte globulins. Transplantation, 75: 657-662, 2003.
30. Siegel, S. and Castellan, N. J. Non parametric statistics for the behavioral sciences. New York: McGraw-Hill, 1988.
31. Sebo, P., Moukrim, Z., Kalhous, M., Schaft, N., Dadaglio, G., Sheshko, V., Fayolle, C., and Leclerc, C. In vivo induction of CTL responses by recombinant adenylate cyclase of *Bordetella pertussis* carrying multiple copies of a viral CD8(+) T-cell epitope. FEMS Immunol Med Microbiol, 26: 167-173, 1999.
32. Matsui, S., Ahlers, J. D., Vortmeyer, A. O., Terabe, M., Tsukui, T., Carbone, D. P., Liotta, L. A., and Berzofsky, J. A. A model for CD8+ CTL tumor immunosurveillance and regulation of tumor escape by CD4 T cells through an effect on quality of CTL. J Immunol, 163: 184-193, 1999.
33. Romagnani, S. Th1 and Th2 in human diseases. Clin Immunol Immunopathol, 80: 225-235, 1996.
34. Greenstone, H. L., Nieland, J. D., de Visser, K. E., De Bruijn, M. L., Kirnbauer, R., Roden, R. B., Lowy, D. R., Kast, W. M., and Schiller, J. T. Chimeric papillomavirus virus-like particles elicit antitumor immunity against the E7 oncoprotein in an HPV16 tumor model. Proc Natl Acad Sci USA, 95: 1800-1805, 1998.
35. De Bruijn, M. L., Schuurhuis, D. H., Vierboom, M. P., Vermeulen, H., de Cock, K. A., Ooms, M. E., Ressing, M. E., Toebes, M., Franken, K. L., Drijfhout, J. W., Ottenhoff, T. H., Offringa, R., and Melief, C. J. Immunization with human papillomavirus type 16 (HPV16) oncoprotein-loaded dendritic cells as well as protein in adjuvant induces MHC class I-restricted protection to HPV16-induced tumor cells. Cancer Res, 58: 724-731, 1998.
36. El Azami El Idrissi, M., Ladant, D., and Leclerc, C. The adenylate cyclase of *Bordetella pertussis*: a vector to target antigen presenting cells. Toxicon, 40: 1661-1665, 2002.
37. Zwaveling, S., Ferreira Mota, S. C., Nouta, J., Johnson, M., Lipford, G. B., Offringa, R., van der Burg, S. H., and Melief, C. J. Established human papillomavirus type 16-expressing tumors are effectively eradicated following vaccination with long peptides. J Immunol, 169: 350-358, 2002.
38. Knutson, K. L., Schiffman, K., and Disis, M. L. Immunization with a HER-2/neu helper peptide vaccine generates HER-2/neu CD8 T-cell immunity in cancer patients. J Clin Invest, 107: 477-484, 2001.
39. Karimova, G., Fayolle, C., Gmira, S., Ullmann, A., Leclerc, C., and Ladant, D. Charge-dependent translocation of *Bordetella pertussis* adenylate cyclase toxin into eukaryotic cells: implication for the in vivo delivery of CD8(+) T cell epitopes into antigen-presenting cells. Proc Natl Acad Sci USA, 95: 12532-12537, 1998.
40. van der Burg, S. H., Kwappenberg, K. M., O'Neill, T., Brandt, R. M., Melief, C. J., Hickling, J. K., and Offringa, R. Pre-clinical safety and efficacy of TA-CIN, a recombinant HPV16 L2E6E7 fusion protein vaccine, in homologous and heterologous prime-boost regimens. Vaccine, 19: 3652-3660, 2001.

41. Chu, N. R., Wu, H. B., Wu, T., Boux, L. J., Siegel, M. I., and Mizzen, L. A. Immunotherapy of a human papillomavirus (HPV) type 16 E7-expressing tumour by administration of fusion protein comprising *Mycobacterium bovis* bacille Calmette-Guerin (BCG) hsp65 and HPV16 E7. Clin Exp Immunol, 121: 216-225, 2000.
42. Bourgeois, C., Rocha, B., and Tanchot, C. A role for CD40 expression on CD8+ T cells in the generation of CD8+ T cell memory. Science, 297: 2060-2063, 2002.
43. Glaser, P. et al, 1988, The calmodulin-sensitive adenylate cyclase of *Bordetella pertussis*: cloning and expression in *E. coli* Molecular Microbiology 2(1), 19-30.
44. Sebo P. et al, 1995, Cell-invasive activity of epitope-tagged adenylate cyclase of *Bordetella pertussis* allows in vitro presentation of a foreign epitope to CD8+ cytotoxic T cells. Infection and Immunity, p. 3851-3857.
45. El-Azami-El-Idrissi M. et al, 2003 Oct. 3, Interaction of *Bordetella pertussis* adenylate cyclase with CD11b/CD18: Role of toxin acylation and identification of the main integrin interaction domain. J. Biol. Chem. 278 (40): 38514-21.
46. Kast, W. M. et al, 1994, Role of HLA-A motifs in identification of potential CTL epitopes in human papillomavirus type 16 E6 and E7 proteins, J. Immunol, 152: 3904-3912.
47. Courret N, Lang T, Milon G, Antoine J C. Intradermal inoculations of low doses of *Leishmania major* and *Leishmania amazonensis* metacyclic promastigotes induce different immunoparasitic processes and status of protection in BALB/c mice. Int J Parasitol 2003; 33:1373-83.
48. Chu N R, Wu H B, Wu T, Boux L J, Siegel M I, Mizzen L A. Immunotherapy of a human papillomavirus (HPV) type 16 E7-expressing tumour by administration of fusion protein comprising *Mycobacterium bovis* bacille Calmette-Guerin (BCG) hsp65 and HPV16 E7. Clin Exp Immunol 2000; 121:216-25.

The invention claimed is:

1. A therapeutic vaccine composition, comprising at least one chimeric recombinant *Bordetella* sp. adenylate cyclase (CyaA) protein or fragment thereof, the CyaA protein or fragment thereof comprising at least one inserted human papilloma virus (HPV) E7 epitope, wherein administering the therapeutic vaccine composition to a mammalian subject infected with HPV prevents HPV-induced tumor growth in the subject.

2. The therapeutic vaccine composition of claim 1, wherein administering the therapeutic vaccine composition to the mammalian subject reduces HPV induced tumor growth in the subject.

3. The therapeutic vaccine composition of claim 1, wherein administering the therapeutic vaccine composition to the mammalian subject causes regression of an HPV induced tumor in the subject.

4. The therapeutic vaccine composition of claim 1, wherein administering the therapeutic vaccine composition to the mammalian subject protects against the onset of malignant transformation by HPV in the subject.

5. The therapeutic vaccine composition of claim 1, wherein the chimeric recombinant CyaA protein or fragment thereof retains the property of the CyaA protein to target CD11b/CD18 Antigen Presenting Cells (APC).

6. The therapeutic vaccine composition of claim 1, wherein the chimeric recombinant CyaA protein or fragment thereof retains the property of the CyaA protein to cause translocation of the at least one inserted HPV E7 epitope into the cytosol of targeted cells in the subject.

7. The therapeutic vaccine composition of claim 1, wherein the at least one inserted HPV E7 epitope is from an oncogenic HPV selected from oncogenic HPV16, HPV18, HPV31, HPV33, HPV35, HPV45, HPV52, and HPV58.

8. The therapeutic vaccine composition of claim 1, wherein the at least one inserted HPV E7 epitope is from HPV16.

9. The therapeutic vaccine composition of claim 1, wherein the at least one inserted HPV E7 epitope is from HPV18.

10. The therapeutic vaccine composition of claim 1, wherein the chimeric recombinant CyaA protein or fragment thereof comprises from about 30 to about 1300 amino acid residues of the CyaA protein, wherein the about 30 to about 1300 amino acid residues comprise at least one fragment selected from amino acid residues 1208 to 1243 of the CyaA protein of *Bordetella pertussis* and amino acid residues 1188 to 1281 of the CyaA protein of *Bordetella pertussis*.

11. The therapeutic vaccine composition of claim 1, wherein the chimeric recombinant CyaA protein or fragment thereof does not comprise amino acid residues 225 to 234 of the CyaA protein.

12. The therapeutic vaccine composition of claim 1, wherein the chimeric recombinant CyaA protein or fragment thereof comprises an inserted polypeptide comprising from about 5 to about 500 amino acid residues that comprises the at least one inserted HPV E7 epitope.

13. The therapeutic vaccine composition of claim 1, wherein the chimeric recombinant CyaA protein or fragment thereof comprises an inserted polypeptide comprising from about 5 to about 200 amino acid residues that comprises the at least one inserted HPV E7 epitope.

14. The therapeutic vaccine composition of claim 1, wherein the chimeric recombinant CyaA protein or fragment thereof comprises an inserted polypeptide comprising from about 10 to about 50 amino acid residues that comprises the at least one inserted HPV E7 epitope.

15. The therapeutic vaccine composition of claim 1, wherein the chimeric recombinant CyaA protein or fragment thereof is obtained by insertion of at least two fragments of the native E7 protein in at least two permissive sites of the CyaA protein or fragment thereof, wherein the orientation of the at least two inserted fragments is reversed with respect to their natural location in the E7 protein.

16. The therapeutic vaccine composition of claim 1, wherein the chimeric recombinant CyaA protein or fragment thereof comprises an inserted polypeptide comprising residues 1 to 29 of the E7 protein of HPV16, or comprising residues 43 to 98 of E7 protein of HPV16, or both fragments inserted in different permissive sites.

17. The therapeutic vaccine composition of claim 1, wherein the chimeric recombinant CyaA protein or fragment thereof comprises an inserted polypeptide comprising at least one sequence selected from amino acid sequence RAHYNIVTF (SEQ ID NO: 1) ($E7_{49-57}$) and amino acid sequence GQAEPDRAHYNIVTFCCKCDSTLRL-CVQSTHVDIR (SEQ ID NO: 2) ($E7_{43-77}$).

18. The therapeutic vaccine composition of claim 1, wherein the CyaA protein or fragment thereof is the *Bordetella pertussis* CyaA protein or a fragment thereof.

19. The therapeutic vaccine composition of claim 1, wherein the enzymatic activity of the CyaA protein or fragment thereof has been inactivated.

20. The therapeutic vaccine composition of claim 19, wherein the enzymatic activity of the CyaA protein or fragment thereof has been genetically inactivated.

21. The therapeutic vaccine composition of claim 20, wherein the enzymatic activity of the CyaA protein or fragment thereof has been genetically inactivated as a result of a dipeptide inserted in a site of the amino acid sequence of CyaA involved in cyclase activity.

22. The therapeutic vaccine composition of claim 21, wherein the dipeptide is inserted into the CyaA protein or fragment thereof between residues 188 and 189 of the native CyaA protein.

23. The therapeutic vaccine composition of claim 1, wherein the chimeric recombinant CyaA protein is encoded by the insert contained in plasmid pTRACE5-HPV16E7$_{FULL}$ (C.N.C.M. 1-3191).

24. The therapeutic vaccine composition of claim 1, wherein the chimeric recombinant CyaA protein is encoded by the insert contained in plasmid pTRACE5-HPV16E7$_{\Delta 30\_42}$ (C.N.C.M. 1-3190).

25. The therapeutic vaccine composition of claim 1, wherein the vaccine composition elicits a cell-mediated immune response when administered to a mammalian subject.

26. The therapeutic vaccine composition of claim 1, wherein the vaccine composition elicits a humoral immune response when administered to a mammalian subject.

27. The therapeutic vaccine composition of claim 1, further comprising at least one of a physiologically acceptable vehicle, a physiologically acceptable excipient, a physiologically acceptable carrier, and a physiologically acceptable diluent.

28. The therapeutic vaccine composition of claim 1, further comprising at least one of an adjuvant, a surfactant, and an immunomodulating substance.

29. The therapeutic vaccine composition of claim 1, wherein the chimeric recombinant CyaA protein or fragment thereof comprises at least two E7 epitopes inserted in different permissive sites.

30. The therapeutic vaccine composition of claim 29, wherein the at least two inserted E7 epitopes are a fragment of the E7 protein of HPV 16 and a fragment of the E7 protein of HPV18.

31. The therapeutic vaccine composition of claim 29, wherein the at least two inserted E7 epitopes are fragments of the E7 protein of HPV 16.

32. The therapeutic vaccine composition of claim 29, wherein the at least two inserted E7 epitopes are fragments of the E7 protein of HPV18.

33. The therapeutic vaccine composition of claim 31, wherein at least one of the fragments of the E7 protein of HPV16 is selected from a fragment comprising the first 29 amino acid residues of HPV16-E7 inserted into the CyaA protein or fragment thereof between residues 319 and 320 of the native CyaA protein and a fragment comprising amino acid residues 43 to 98 of HPV16-E7 inserted into the CyaA protein or fragment thereof between residues 224 and 235 of the native CyaA protein.

34. The therapeutic vaccine composition of claim 33, wherein the chimeric recombinant CyaA protein or fragment thereof comprises the fragment comprising the first 29 amino acid residues of HPV16-E7 inserted between residues 319 and 320 of the native CyaA protein and the fragment comprising amino acid residues 43 to 98 of HPV16-E7 inserted between residues 224 and 235 of the native CyaA protein.

35. The therapeutic vaccine composition of claim 32, wherein at least one of the fragments of the E7 protein of HPV18 is selected from a fragment comprising the first 31 amino acid residues of HPV18-E7 inserted into the CyaA protein or fragment thereof between residues 319 and 320 of the native CyaA protein and a fragment comprising amino acid residues 43 to 105 of HPV 18-E7 inserted into the CyaA protein or fragment thereof between residues 224 and 235 of the native CyaA protein.

36. The therapeutic vaccine composition of claim 35, wherein the CyaA protein or fragment thereof comprises the fragment comprising the first 31 amino acid residues of HPV18-E7 inserted between residues 319 and 320 of the native CyaA protein and the fragment comprising amino acid residues 43 to 105 of HPV 18-E7 inserted between residues 224 and 235 of the native CyaA protein.

37. The therapeutic vaccine composition of claim 1, comprising at least two different chimeric recombinant CyaA proteins or fragments thereof.

38. The therapeutic vaccine composition of claim 37, wherein the first of the at least two chimeric recombinant CyaA proteins or fragments thereof comprises a fragment of the E7 protein of HPV16 selected from a fragment comprising the first 29 amino acid residues of HPV16-E7 inserted between residues 319 and 320 of the native CyaA protein and a fragment comprising amino acid residues 43 to 98 of HPV16-E7 inserted between residues 224 and 235 of the native CyaA protein; and wherein the second of the at least two chimeric recombinant CyaA proteins or fragments thereof comprises a fragment of the E7 protein of HPV18 selected from a fragment comprising the first 31 amino acid residues of HPV18-E7 inserted between residues 319 and 320 of the native CyaA protein and a fragment comprising amino acid residues 43 to 105 of HPV 18-E7 inserted between residues 224 and 235 of the native CyaA protein.

39. The therapeutic vaccine composition of claim 38, wherein the first of the at least two CyaA proteins or fragments thereof comprises the fragment comprising the first 29 amino acid residues of HPV16-E7 inserted between residues 319 and 320 of the native CyaA protein and comprises the fragment comprising amino acid residues 43 to 98 of HPV16-E7 inserted between residues 224 and 235 of the native CyaA protein; and wherein the second of the at least two CyaA proteins or fragments thereof comprises the fragment comprising first 31 amino acid residues of HPV18-E7 inserted between residues 319 and 320 of the native CyaA protein and the fragment comprising amino acid residues 43 to 105 of HPV 18-E7 inserted between residues 224 and 235 of the native CyaA protein.

40. The therapeutic vaccine composition of claim 29, wherein the chimeric recombinant CyaA protein or fragment thereof comprises residues 43 to 98 of HPV16-E7 followed by residues 43 to 105 of HPV18-E7 inserted between residues 224 and 235 of the native CyaA protein and the first 31 amino acid residues of HPV18-E7 followed by the first 29 amino acid residues of HPV16-E7 inserted between residues 319 and 320 of the native CyaA protein.

41. The therapeutic vaccine composition of claim 22, wherein the CyaA protein or fragment thereof is enzymatically inactivated by insertion of a LQ dipeptide between amino acid residues Asp 188 and Ile 189 of the native CyaA protein.

42. The therapeutic vaccine composition of claim 1, wherein the at least one inserted HPV E7 epitope has been modified with respect to its native amino acid sequence by addition of non-naturally flanking sequences.

43. The therapeutic vaccine composition of claim 1, wherein the subject is a human.

* * * * *

UNITED STATES PATENT AND TRADEMARK OFFICE
CERTIFICATE OF CORRECTION

PATENT NO. : 8,628,779 B2
APPLICATION NO. : 11/517313
DATED : January 14, 2014
INVENTOR(S) : Preville et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1486 days.

Signed and Sealed this
Thirtieth Day of May, 2017

Michelle K. Lee
*Director of the United States Patent and Trademark Office*

```
                          SEQUENCE LISTING

<160> NUMBER OF SEQ ID NOS: 26

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala His Tyr Asn Ile Val Thr Phe
  1               5

<210> SEQ ID NO 2
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gln Ala Glu Pro Asp Arg Ala His Tyr Asn Ile Val Thr Phe Cys
  1               5                  10                  15

Cys Lys Cys Asp Ser Thr Leu Arg Leu Cys Val Gln Ser Thr His Val
             20                  25                  30

Asp Ile Arg
         35

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Asp Gly Val Asn His Gln His Leu
  1               5

<210> SEQ ID NO 4
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 4

Ala Ser Gly Val Asn His Gln His Leu
 1               5

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctagccgtgc ccattacaat attgtaacct ttggtac                              37

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caaaggttac aatattgtaa tgggcacgg                                       29

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggcgctagc atgcatggag atacacctac                                      30

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggcggtacc tggtttctga gaacagatgg g                                    31

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gggcaccggt aaacgtatgc acggcgatac tccg                                 34

<210> SEQ ID NO 10
<211> LENGTH: 48
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 10
cgtgagcatc tggctttcac tagtacgttt gttcagctgc tcgtagca                    48

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggcactagt gaaagccaga tgctcacgcg cggg                                   34

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agtacatccg gcgagaac                                                     18

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gggcgctagc ggtcaagcag aaccggac                                          28

<210> SEQ ID NO 14
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggcggtacc aggtttttga gagcaaatcg gacaaacaat ccccagagta cccatc           56

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Ile Ile Asn Phe Glu Lys Leu
 1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 16

Asp Arg Ala His Tyr Asn Ile Val Thr Phe
 1               5                  10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Ser Ser Glu Glu Glu Asp Glu Ile Asp Gly Pro Ala
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Met Leu Asp Leu Gln Pro Glu Thr Thr
 1               5                  10

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Leu Met Gly Thr Leu Gly Ile Val
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Leu Gly Ile Val Cys Pro Ile
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Leu Gln Asp Ile Val Leu His Leu
 1               5

<210> SEQ ID NO 22
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Gln Gln Leu Phe Leu Asn Thr Leu
  1               5

<210> SEQ ID NO 23
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met His Gly Asp Thr Pro Thr Leu His Glu Tyr Met Leu Asp Leu Gln
  1               5                  10                  15

Pro Glu Thr Thr Asp Leu Tyr Cys Tyr Glu Gln Leu Asn Asp Ser Ser
             20                  25                  30

Glu Glu Glu Asp Glu Ile Asp Gly Pro Ala Gly Gln Ala Glu Pro Asp
         35                  40                  45

Arg Ala His Tyr Asn Ile Val Thr Phe Cys Cys Lys
     50                  55                  60

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Asp Ser Thr Leu Arg Leu Cys Val Gln Ser Thr His Val Asp Ile
  1               5                  10                  15

Arg Thr Leu Glu Asp Leu Leu Met Gly Thr Leu Gly Ile Val Cys Pro
             20                  25                  30

Ile Cys Ser Gln Lys Pro
         35

<210> SEQ ID NO 25
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gln Ala Glu Pro Asp Arg Ala His Tyr Asn Ile Val Thr Phe Cys
  1               5                  10                  15

Cys Lys Cys Asp Ser Thr Leu Arg Leu Cys Val Gln Ser Thr His Val
             20                  25                  30

Asp Ile Arg Thr Leu Glu Asp Leu Leu Met Gly Thr Leu Gly Ile Val
         35                  40                  45

Cys Pro Ile Cys Ser Gln Lys Pro
     50                  55

<210> SEQ ID NO 26
<211> LENGTH: 29
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn
                20                  25
```